United States Patent [19]

Beeby

[11] 4,112,087
[45] Sep. 5, 1978

[54] CEPHALOSPORIN TYPE ANTIBACTERIALS HAVING A SUBSTITUTED PROPENYL GROUP IN THE 3-POSITION

[75] Inventor: Philip J. Beeby, Melbourne, Australia

[73] Assignee: Syntex (U.S.A.) Inc., Palo Alto, Calif.

[21] Appl. No.: 738,776

[22] Filed: Nov. 4, 1976

[51] Int. Cl.$^2$ .................... C07D 501/24; A61K 31/38
[52] U.S. Cl. ..................... 424/246; 542/413; 542/426; 544/16; 544/22; 544/29
[58] Field of Search ............. 260/243 C; 544/16, 22, 544/29; 542/426, 413; 424/246

[56] References Cited

U.S. PATENT DOCUMENTS

| 3,769,277 | 10/1973 | Long et al. | 260/243 C |
| 3,830,700 | 8/1974 | O'Callaghan et al. | 544/16 |
| 3,929,780 | 12/1975 | Weir | 260/243 C |
| 3,983,113 | 9/1976 | Beeby | 542/413 |
| 3,994,884 | 11/1976 | Wein | 544/16 |
| 4,012,380 | 3/1977 | Spry | 260/243 C |
| 4,012,381 | 3/1977 | Foglio et al. | 260/243 C |
| 4,049,806 | 9/1977 | Beeby | 544/22 |

OTHER PUBLICATIONS

Beeby, U.S. Patent Application, S.N. 709,696, 7-29-76.

Primary Examiner—Donald G. Daus
Assistant Examiner—Mary C. Vaughn
Attorney, Agent, or Firm—Richard J. Hammond; Gerard A. Blaufarb

[57] ABSTRACT

Compounds of the formula

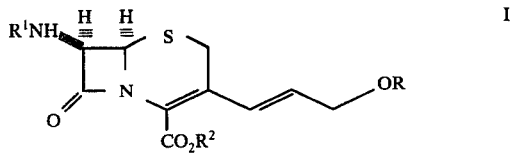

wherein R is alkyl having 1 to 4 carbon atoms, $\beta$-haloethyl, allyl, propargyl, cyclopentyl or benzyl; $R^1$ is hydrogen or an $\alpha$-substituted acetamido group; $R^2$ is hydrogen or a protecting group; and the pharmaceutically acceptable salts thereof. The 7$\beta$-amino compounds are useful as intermediates for the 7$\beta$-($\alpha$-substituted acetamido) compounds which are useful as antibacterials against a wide variety of gram positive and gram negative bacteria.

34 Claims, No Drawings

CEPHALOSPORIN TYPE ANTIBACTERIALS HAVING A SUBSTITUTED PROPENYL GROUP IN THE 3-POSITION

BACKGROUND OF THE INVENTION

1. The Invention

This invention relates to cephalosporin type compounds, having antibacterial activity and intermediates and processes for preparing such compounds. More particularly, the present invention relates to compounds having the formula

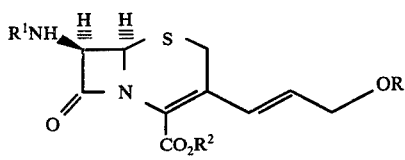

wherein;

R is alkyl having 1 to 4 carbon atoms, β-haloethyl, allyl, propargyl, cyclopentyl or benzyl;

$R^1$ is hydrogen or a group having the formula

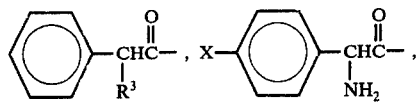

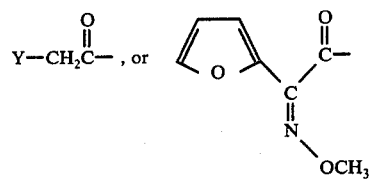

wherein $R^3$ is hydrogen, hydroxy or carboxy; X is hydrogen or hydroxy; Y is thiophen-2-yl, (1H)-tetrazol-1-yl, 4-pyridylthio, phenoxy, trifluoromethylthio, 4-nitrophenyl or 3-chlorophenyl;

$R^2$ is hydrogen or a protecting group selected from the group of benzhydryl, benzyl, o-nitrobenzyl, p-nitrobenzyl, 3,5-dinitrobenzyl, p-methoxybenzyl, tert-butyl, pivaloyloxymethyl, phenacyl and polyhaloalkyl having 2 to 6 carbon atoms; and the pharmaceutically acceptable salts thereof; and to intermediates for, and methods of preparing such compounds. In a still further aspect, the invention relates to pharmaceutical compositions and antiseptic compositions containing such compounds and to methods of destroying and/or inhibiting the growth of gram negative and/or gram positive bacteria.

2. The Prior Art

Since the first discovery that certain derivatives of Cephalosporin exhibit potent antibiotic activity, a large number of cephalosporin type compounds have been synthesized for possible improved, or different, antibiotic activity and selectivity (note for example, U.S. Pat. Nos. 3,769,277, 3,830,700, 3,853,860, 3,859,274, 3,864,338 and 3,867,380). A general discussion of cephalosporins can be found in *Cephalosporins and Penicillins Chemistry and Biology*, edit E. H. Flynn, Academic Press, Inc. (1972).

SUMMARY OF THE INVENTION

In summary, the compounds of the invention can be represented by the following generic formula:

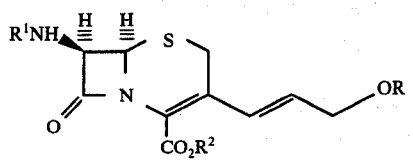

wherein;

R is alkyl having 1 to 4 carbon atoms, β-haloethyl, allyl, propargyl, cyclopentyl, or benzyl;

$R^1$ is hydrogen or a group having the formula

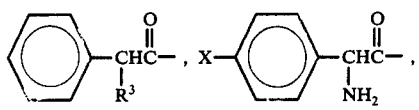

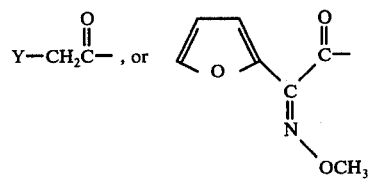

wherein $R^3$ is hydrogen, hydroxy or carboxy; X is hydrogen or hydroxy; Y is thiophen-2-yl, (1H)-tetrazol-1-yl, 4-pyridylthio, phenoxy, trifluoromethylthio, 4-nitrophenyl or 3-chlorophenyl;

$R^2$ is hydrogen or a protecting group selected from the group of benzhydryl, benzyl, o-nitrobenzyl, p-nitrobenzyl, 3,5-dinitrobenzyl, p-methoxybenzyl, tert-butyl, pivaloyloxymethyl, phenacyl and polyhaloalkyl having 2 to 6 carbon atoms.

The pharmaceutically acceptable salts of the above compounds wherein $R^1$ is other than hydrogen, with respect to the C-4 acid and $R^3$ moieties, are also encompassed within the scope of the invention. Also, as can be seen from Formula I, the steric configuration of the propenyl double bond is trans and the substituent at the 7-position is beta oriented.

In summary, one process of the invention comprises hydrolysing a compound of the formula

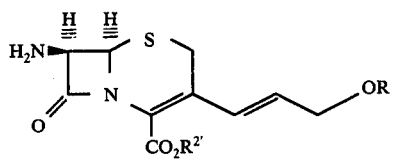

wherein R is as defined above and $R^{2'}$ is as defined above for $R^2$, but is other than hydrogen.

In summary, another process of the invention comprises hydrolysing a compound of the formula

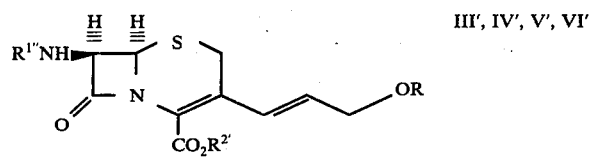  III', IV', V', VI' wherein R and R[2'] are as defined above and R[1''] is as defined above for R[1], but is other than hydrogen, and when α-hydroxy, -carboxy, or -amino functions are present in R[1''], these functions are protected with a suitable protecting group.

In summary, still another process of the invention comprises acylating a compound of the formula

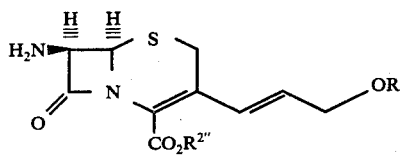  II'' wherein R is as defined above and R[2''] is as defined above for R[2], but is other than a protecting group.

In summary, still yet another process of the invention comprises hydrolysing a compound of the formula

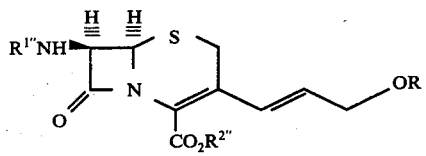  (E)

wherein R, R[1''] and R[2''] are as defined above.

In summary, a further process of the invention comprises optionally converting a free acid of the formula

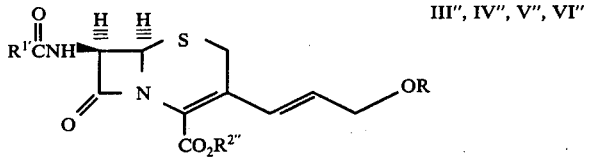  III'', IV'', V'', VI'' wherein R is as defined above, R[1'] is as defined for R[1] but is other than hydrogen and R[2''] is hydrogen, to its corresponding pharmaceutically acceptable salt; or optionally converting a pharmaceutically acceptable salt of a compound of the formula

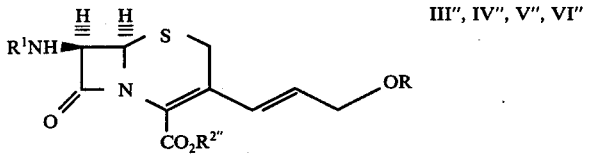  III'', IV'', V'', VI'' wherein R and R[1] are as defined above and R[2''] is a pharmaceutically acceptable cation, its corresponding free acid; or optionally converting a free acid of the formula

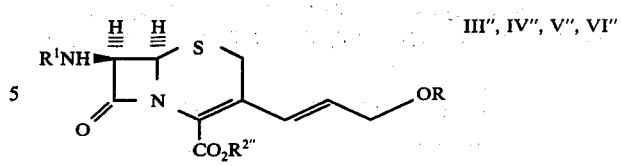  III'', IV'', V'', VI'' or a pharmaceutically acceptable salt thereof, wherein R and R[1] are as defined above and R[2''] is hydrogen or a pharmaceutically acceptable cation, to a suitable ester protecting group.

In summary, the pharmaceutical compositions and antiseptic compositions, of the invention, comprise the 4-carboxylic acid compounds of Formula I, wherein R[1] is other than hydrogen, and/or pharmaceutically acceptable salts thereof, and a pharmaceutical acceptable carrier or antiseptic carrier.

In summary, the process of the invention for reducing or inhibiting bacterial infections comprises administering an effective amount of a carboxylic acid of Formula I, wherein R[1] is other than hydrogen, or a pharmaceutically acceptable salt thereof, to mammals suffering from such infections, or in the case of undesired bacterial growth on inanimate objects, applying an effective amount of the aforementioned compound in an antiseptic carrier to such objects. The invention will be further described hereinbelow.

The invention will be further described hereinbelow.

FURTHER DESCRIPTION OF THE INVENTION AND PREFERRED EMBODIMENTS

The compounds of the invention can be represented by the following sub-generic formulas:

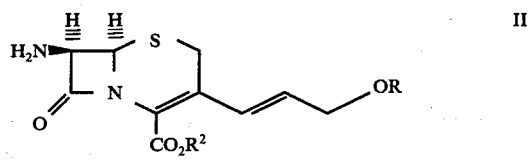  II

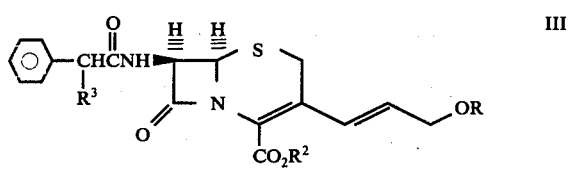  III

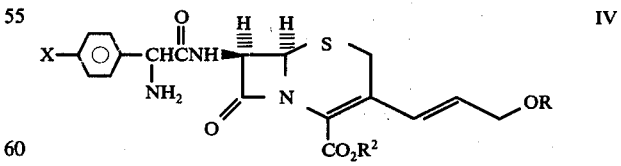  IV

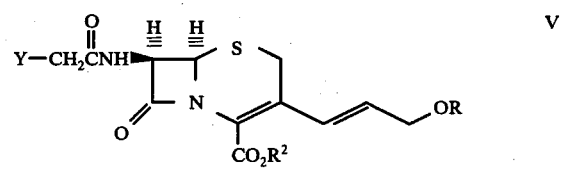  V

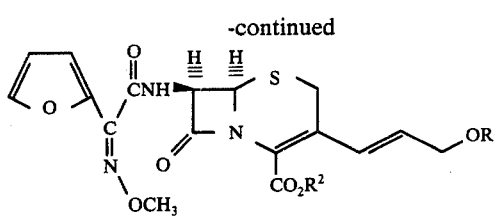

wherein;

R is alkyl having 1 to 4 carbon atoms, β-haloethyl, allyl, propargyl, cyclopentyl or benzyl;

$R^2$ is hydrogen or a protecting group selected from the group of benzhydryl, benzyl, o-nitrobenzyl, p-nitrobenzyl, 3,5-dinitrobenzyl, p-methoxybenzyl, tert-butyl, pivaloyloxymethyl, phenacyl and polyhaloalkyl having 2 to 6 carbon atoms;

$R^3$ is hydrogen, hydroxy or carboxy;

X is hydrogen or hydroxy; and

Y is thiophen-2-yl, (1H)-tetrazol-1-yl, 4-pyridylthio, phenoxy, trifluoromethylthio, 4-nitrophenyl or 3-chlorophenyl.

Also, encompassed within the invention are the pharmaceutically acceptable salts of compounds of formulas III, IV, V and VI.

The compounds of Formula III wherein $R^3$ is hydroxy or carboxy, and the compounds of Formula IV exist as optical isomers; accordingly, the above formulas are intended to represent the respective (D) and (L) optical isomers as well as mixtures thereof and the individual isomers as well as mixtures thereof generally are encompassed within the invention. Generally, in terms of antibiotic activity, the (D) optical isomers at the chiral center in the side chain attached to the 7β-position are preferred.

Also, as previously noted, the C-7 position amino or carbonylamino substituent is beta oriented and the propenyl double bond is trans oriented.

In terms of convenience and ease of preparation, the preferred R substituent is methyl and the preferred $R^2$ protecting group is benzhydryl. In terms of antibiotic activity (compounds of Formulas III, IV, V and VI), the preferred R substituents are allyl, β-bromoethyl and especially methyl; the preferred $R^3$ substituent (III) is carboxy, the preferred X substituent (IV) is hydrogen or hydroxyl, the preferred Y substituent (V) is thiphen-2-yl. The $R^2$ substituent is preferably hydrogen or a pharmaceutically acceptable salt thereof, as the compounds are typically administered as salts.

In terms of convenience, the sodium salts are preferred, correspondingly the particularly preferred salts are the sodium salts of the preferred compounds of Formulas III, IV, V and VI. The preferred compounds of Formula II are the corresponding precursors of the preferred compounds of Formulas III, IV, V, and VI.

The process of preparing the compounds of the invention can be schematically represented by the following sequence of overall reaction equations:

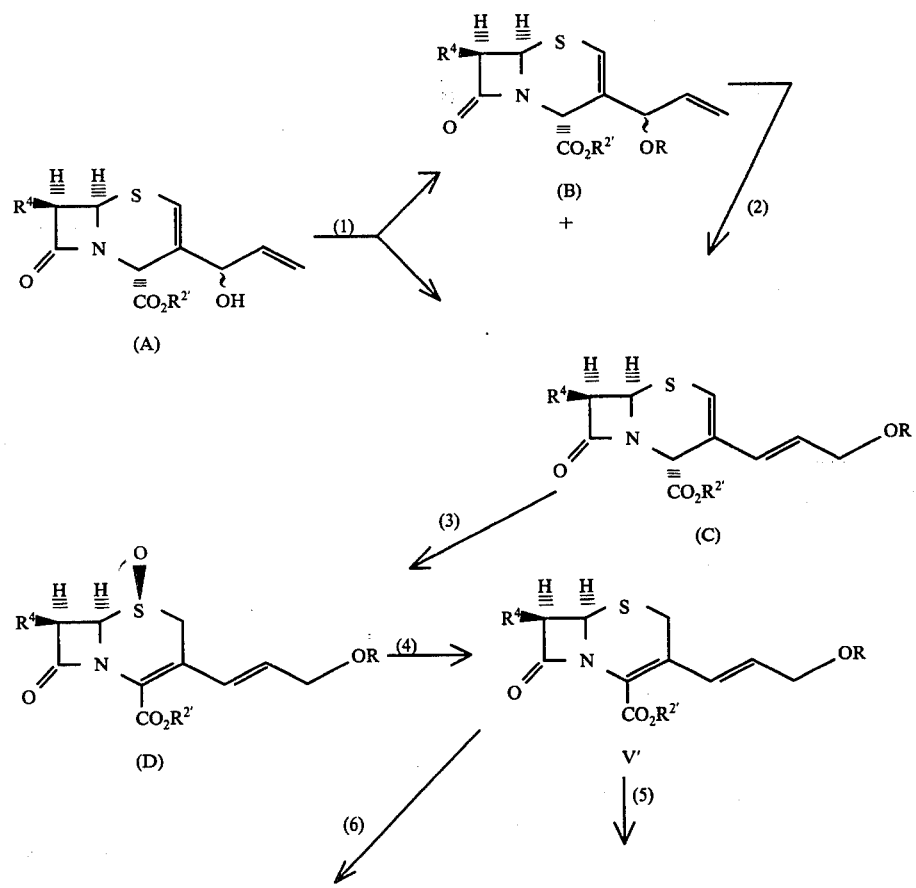

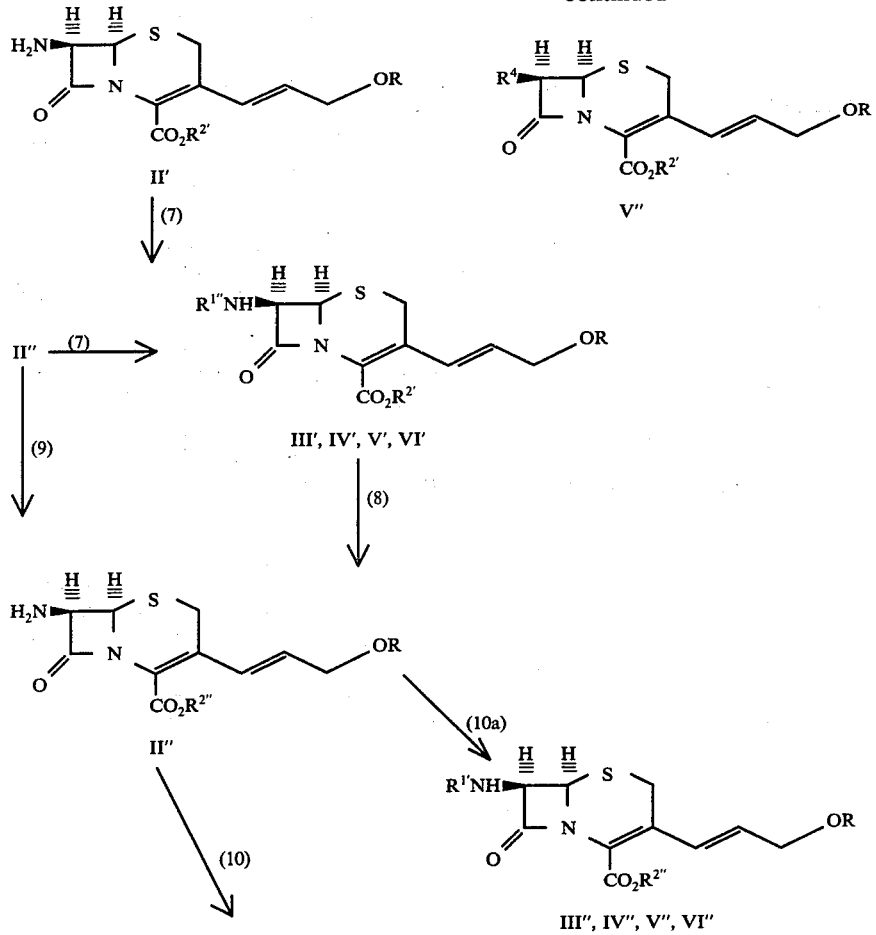

wherein R is as defined above; $R^{1'}$ is as defined above for $R^1$, but is other than hydrogen; $R^{1''}$ is as defined above for $R^1$, but is other than hydrogen, and when α-hydroxy, -carboxy or -amino functions are present in $R^{1''}$, these functions are protected with a suitable protecting group; $R^{2'}$ is a suitable protecting group, e.g. benzhydryl; $R^{2''}$ is hydrogen or a pharmaceutically acceptable cation, e.g., sodium; $R^4$ is the group

and the ~ OH and ~ OR in Formulas A and B, respectively, indicate a mixture of α and β isomers.

Step 1, of the process can be conveniently effected by treating the starting material of Formula a with a suitable alcohol corresponding to the desired R substituent, in the presence of an acid (e.g., typically about 0.01 to 0.05 moles of acid per mole of the compound of Formula A). This treatment is optionally conducted in the presence of a polar organic solvent at temperatures in the range of about from −40° to 50° C, preferably at about 0° C for about from 30 minutes to six hours, preferably abut four hours, using mole ratios of alcohol to compound of Formula A of about from 1 to 50, preferably about from 5 to 25. Suitable polar organic solvents which can be used include, acetonitrile, dimethoxyethane, dioxane, methylene chloride and tetrahydrofuran. Suitable inorganic acids which can be used include, sulfuric acid, hydrobromic acid, phosphoric acid, tetrafluoroboric acid, and perchloric acid. Suitable organic acids which can be used include, p-toluenesulfonic acid and p-nitrobenzenesulfonic acid. The products of formulas B and C can be separated by chromatography, for instance on silica gel, eluting with methylene chloride containing 1–10% acetone.

Step 2, rearrangement of the 1-substituted-prop-2-enyl group to a 3-substituted-prop-1-(t)-enyl group, can be effected by treating the compound of Formula B in the manner described in the previous paragraph, however, treatment in this instance is conducted at temperatures in the range of about from 20° to 60° C, preferably at about 25° C, for about from 12 to 72 hours, preferably about 48 hours.

Step 3, can be conveniently effected by treating the compound of Formula C with m-chloroperbenzoic acid in a suitable inert organic solvent. Typically, this treatment is conducted at temperatures in the range of about from −0° to 25° C, preferably about from 0° to 5° C for about from 0.5 to 24 hours, preferably about from 3 to 5 hours, using mole ratios of m-chloroperbenzoic acid to compound of Formula C of about from 1.0 to 1.2. Preferably this mole ratio should be close to 1(about from 1.05 to 1.1) to prevent over oxidation of the sulfoxide moiety to sulfonyl. Suitable inert organic solvents which can be used, include for example, methylene chloride, chloroform, and the like, and mixtures thereof. Also, in place of m-chloroperbenzoic acid, the following reagents could also be used: perbenzoic acid, peracetic acid, hydrogen peroxide, sodium metaperiodate, ozone, and the like.

Step 4, can be conveniently effected by treating the sulfoxide of Formula D with a mixture of stannous chloride and acetyl chloride in a suitable organic solvent, preferably under an inert atmosphere. Typically, this treatment is conducted at temperatures in the range of about from −10° to 25° C, preferably to 0° to 5° C for about from 0.25 to 5.0 hours, preferably about from 1.0 to 2 hours, using mole ratios of stannous chloride to compound of Formula D of about from 1.5 to 5.0, and preferably about from 2.0 to 3.0. Also, in place of stannous chloride and acetyl chloride, the following reagents could also be used: phosphorous trichloride, phosphorous tribromide, and the like and mixtures thereof.

Step 5, can be effected by conventional procedures used in the art to cleave ester groups to yield the corresponding free acid. For example, C-4 benzhydryl and p-methoxybenzyl groups can be conveniently cleaved via treatment with a trifluoroacetic acid/anisole mixture (typically 2:1 to 6:1 mole ratios) at 0° to 5° C for about from 2 to 5 minutes optionally in the presence of an inert solvent such as methylene chloride, benzene, and the like.

Step 6 of the process is effected by treating the compound of Formula V' with phosphorus pentachloride in an inert organic solvent in the presence of pyridine. The first part of this treatment is typically conducted under anhydrous conditions and under an inert atmosphere at temperatures in the range of about fro 10° to 30° C for about from 2 to 4 hours using 1.1 to 1.2 moles of pyridine and about from 1.1 to 1.2 moles of phosphorus pentachloride per mole of compound of Formula V'. After the resulting reaction is substantially complete, about from 2 to 10 moles of isobutyl alcohol, preferably about 5 moles of isobutyl alcohol per mole of Formula V', is added to the product mixture, and the treatment is then continued at temperatures in the range of about from a −20° to 30° C, preferably from about 0° to 5° C, for about from 15 minutes to 2 hours, preferably about from 30 minutes to 1 hour. A small quantity of water is then added to effect the final reaction in this treatment. This final step is typically conducted at temperatures in the range of −20° to 30° C, preferably about from 0° to 5° C for about from 5 minutes to 1 hour, preferably about from 15 minutes to 30 minutes. Suitable inert organic solvents which can be used for this treatment include, for example, chloroform and the like. Also, in place of pyridine, the following compounds could, for example, be used: quinoline, N,N-dimethylaniline, and the like. Also, in place of isobutyl alcohol, other lower alkanols could be used, for example, methanol, ethanol, and the like or mixtures thereof.

The next steps in the process, i.e., acylation of the amino group and, if desired, removal of the C-4 ester group can be conducted interchangeably. Thus, the C-4 ester group can first be cleaved (Step 9) and then the amino group acylated (Step 10 or Step 10a) or vice versa (i.e., Steps 7 and 8). Steps 7, 10 and 10a, acylation of the C-7 amino group can be effected by conventional amino acylation procedures. For example, Steps 7, 10 and 10a can be conveniently effected by treating compounds of Formulas II' and II'' with from about 1.1 to 1.5 stoichiometric equivalents of a suitable acyl halide, having the desired acyl moiety in an inert organic solvent (e.g., dichloromethane, chloroform, etc.) in the presence of an organic or inorganic base (e.g., sodium bicarbonate, pyridine, triethylamine and the like) at temperatures in the range of about from 0° to 5° C for about from 30 minutes to 1 hour. Typically, about from 2 to 10 stoichiometric equivalents of the base is used. The acylation can also be effected via treatment with a carboxy acid, having the desired acyl moiety, and a suitable coupling reagent, e.g., dicyclohexyl carbodiimide or N-ethoxycarbonyl-2-ethoxy-1,2-dihydroquinoline, in a suitable inert organic solvent, e.g., dichloromethane.

When the acylating agent contains a group of the formula

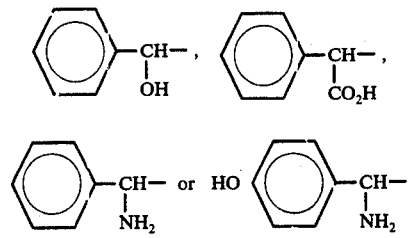

it is preferred that the hydroxy, carboxy and amino functions in the group be protected with a suitable protecting group which can be easily removed at a later stage.

For example, α-hydroxy compounds can be conveniently prepared via acylation with an α-dichloroacetoxyphenylacetyl halide or acid to yield the corresponding protected hydroxy derivative. Similarly, α-carboxy compounds can be prepared via acylation with an α-(tert-butoxycarbonyl)-α-phenylacetyl halide or acid to yield the corresponding tert-butyl protected α-carboxy derivative. In like manner, α-amino compounds can be prepared via acylation with an α-(tert-butoxycarbonylamino)-α-phenylacetyl halide or acid to yield the corresponding tert-butoxycarbonyl protected α-amino derivative.

If the optical isomers of compounds of Formulas III'' and IV'' (wherein $R^4$ is hydroxy, carboxy or amino) are desired, they can be conveniently prepared by using the corresponding optically active acid halide or acid in the acylation step. In the case of compounds of Formula III'' wherein $R^4$ is carboxy, a reaction equilibrium exists between the respective D and L optical isomers and hence in this case the stable compound will exist as a mixture of the D and L isomers.

Removal of the C-4 ester group and/or deprotection, if necessary, of the $R^{1'''}$ moiety of the 7β-substituent is effected in Steps 8, 9 and 11.

A. Removal of the C-4 ester group in compounds of Formulas II', III' ($R^3$=H), V' and VI' can be effected via steps 8 (II') and 9 (III' where $R^3$=H, V' and VI') by conventional procedures. For example, C-4 benzhydryl and p-methoxybenzyl groups can be cleaved via treatment with a neat trifluoroacetic acid/anisole mixture (typically 2:1 to 6:1 mole ratio) at about 0° to 5° C for about from 2 to 5 minutes or in an inert solvent such as methylene chloride, benzene and the like.

B. Removal off the C-4 ester group and deprotection of the $R^{1''}$ moiety in compounds of Formula III' and E, wherein the 7β-substituent is α-(tert-butoxycarbonyl)-α-phenylacetamido, can be effected via steps 8 (III') and 11 (E) in accordance with the procedure described in paragraph A above, however, the treatment is extended from 2 to 5 minutes to 30 to 120 minutes.

C. Removval of the C-4 ester group and deprotection of the $R^{1''}$ moiety in compounds of Formula III' and E, wherein the 7β-substituent is α-dichloroacetoxy-α-phenylacetamido, can be effected via steps 8 (III') and 11 (E) in accordance with the procedure described in paragraph A above, followed by treatment with aqueous inorganic base, e.g., sodium bicarbonate. Typically, treatment with base is conducted at room temperature for about from 30 minutes to 3 hours using mole ratios of base to compound of Formula III' or E of about from 2 to 20.

D. Removal of the C-4 ester group and deprotection of the $R^{1''}$ moiety in compounds of Formula IV' and E, wherein the 7β-substituent is α-(tert-butoxycarbonylamino)-α-phenylacetamido or 60 -(tert-butoxycarbonylamino)-α-(4-hydroxyphenyl)acetamido can be effected via steps 8 (IV') and 11 (E) in accordance with the procedure described in paragraph B above.

If desired, the C-4 carboxy protecting group can be selectively replaced in compounds of Formulas III'', IV'', V'' and VII'' via conventional procedures; for example, (in the case of benzhydryl protecting groups) by treatment of a compound of Formula III'', IV'', V'' or VI'' with a molar equivalent of diphenyldiazomethane in an inert solvent, such as tetrahydrofuran, ethyl acetate and the like, at 0° to 50° C., preferably about 30° C. for about from 1 to 6 hours, preferably about 3 hours.

It is generally preferred that the respective product of each process step, described hereinabove is separated and/or isolated prior to its use as a starting material in subsequent steps. Separation and isolation can be effect by any suitable purifications procedure such as, for example, evaporation, crystallization, column chromatography, thin-layer chromatography, distillation, etc. Specific illustrations of typical separation and isolation procedures can be had by reference to the appropriate examples described hereinbelow; however, other equivalent separation procedures could, of course, also be used. Also, it should be appreciated that where tupical reaction conditions (e.g., temperatures, mole ratios, reaction times) have been given, that conditions both above and below these ranges can also be used, though generally less conveniently.

The pharmaceutically acceptable salts of the invention, can be prepared according to procedures which are well known in the art, for example, by simply treating the free acid of Formulas III α, IV''', V''' and VI''' with an inorganic or organic base having the desired salt cation; e.g., sodium hydroxide, potassium hydroxide, triethylamine, ethanolamine, tris-(hydroxymethyl)aminomethane etc. The sodium salts can also be conveniently prepared by treating a solution of the acid in a suitable solvent with an excess of sodium 2-ethylhexanoate.

The compounds of the invention and salts thereof, have a broad spectrum of antibacterial activity against both gram positive and gram negative organisms, such as, Staphylococcus aureus Proteus ulgaris, Escherichia coli, Streptococcus pyogenes, Klebsiella pneumoniae, Shigella sonnei. The compounds can be used to combat or prophylactically to prevent infections off this nature in mammals and can be administered in the same manner as cephalothin or cephalosporin derivative drugs are generally administered (typically parenterally or orally). The compounds could be administered in a wide variety of dosage forms, either alone or in combination with other pharmaceutically compatible medicaments, in the form of pharmaceutical compositions suited for oral or parenteral administration. The dosage forms typically comprise the compounds (typically as pharmaceutically acceptable salts) and a pharmaceutically acceptable carrier and a preferably formulated in unit dosage form to facilitate the simple administration of precise dosages. The pharmaceutical carrier can be either a solid material or a liquid, in which the compound is dissolved, dispersed or suspended. The dosage form can optionally contain other compatible medicaments, preservatives, emulsifying agents, wetting agents and/or pH-buffering agents. Suitable preservatives which can be used include, for example, benzyl alcohol and the like. Suitable buffering agents include, for example, sodium acetate and pharmaceutical phosphate salts and the like. Liquid dosage forms include, for example, solutions, suspensions, emulsions, syrups, elixirs, etc. Liquid carriers include, for example, water, saline solution, etc. Solid dosage forms include, for example, tablets, powders capsules, pills, etc. Suitable solid carriers include, for example, pharmaceutical grades of starch, lactose, sodium saccharin, sodium bisulfite and the like.

The compounds of this invention are typically administered in dosages of about from 10 to 100 mg. per kg. per day of body weight. The precise effective dosage will, of course, vary depending on the mode of administration, the condition being treated and the host. The compounds can also be used as antiseptic agents in cleaning or disinfecting compositions, typically in solution form or suspended in a liquid carrier or in an aerosol spray.

Definitions

The following terms as used hereinabove and below, have the following meaning unless expressly stated to the contrary. The term alkyl refers to a saturated, unbranched, or branched acyclic hydrocarbon group containing 1 to 4 carbon atoms, such as methyl, ethyl, n-propyl, isopropyl, n-butyl, tertbutyl, and the like. The term polyhaloalkyl refers to a halo substituted alkyl having from 1 to 6 carbon atoms and containing at least 2 halogen atoms. The term halo or halide refers to fluoro, chloro, bromo or iodo, or the corresponding halides. The term pharmaceutically acceptable salts refers to those salts of the parent compound which do not adversely effect the pharmaceutical properties (e.g., toxicity, effectiveness, etc.) of the parent compound, such as, for example, are conventionally used in the pharmaceutical art. The salts of the present invention are pharmaceutically acceptable cation salts, with respect to the acid moiety and in cases where $R^3$ is carboxy can be prepared both as mono and bis salts. Suitable pharmaceutically acceptable cations include, for example, the alkali metals, e.g., sodium, potassium, etc.; alkaline earth metals, e.g., calcium, etc.; ammonia; organic salts of triethylamine, diethylamine, tris-(hydroxymethyl)aminomethane, ethanolamine, chlorine, caffeine, and the like.

The term benzhydryl refers to the radical having the formula

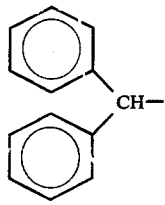

The term (1H)-tetrazol-1-yl refers to the radical having the formula

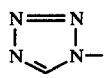

The term 2-methoxyimino-2-(fur-2-yl)acetamido refers to the syn(cis) isomeric form as regards the configuration of the methoxy group with respect to the carboxamido group. In this specification, the syn configuration is structurally denoted thus:

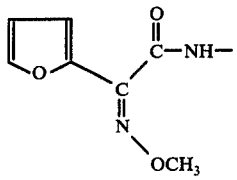

The term room temperature refers to about 20° Centigrade and all temperatures and temperature ranges refer to degrees centigrade. All percents refer to weight percents and the term equivalent mole amount refers to an amount stoichiometrically equivalent to the other reactant in the reaction referred to.

A further understanding of the invention can be had from the following non-limiting preparations and examples. Wherein proton magnetic resonance spectra (n.m.r.) are determined at 100 mHz (the signs of the coupling constants are not assigned) and signals are assigned as singlets (*s*), broad singlets (*bs*), doublets (*d*), double doublets (*dd*), triplets (*t*), double triplets (*dt*), quartets (*q*) and multiplets (*m*).

PREPARATION 1

3-Acetoxymethyl-7β-(thiophen-2-yl-acetamido)-ceph-2-em-4-carboxylic acid

In this preparation 42 g. of cephalothin (i.e., 3-acetoxymethyl-7β-(thiophen-2-yl-acetamido)-ceph-3-em-4-carboxylic acid) is dissolved with warming in 130 ml. pyridine, and then cooled to about 18° C. Acetic anhydride (13 ml.) is added and the resulting mixture allowed to stand for 2 hours at room temperature affording a crystalline precipitate. Then 250 ml. of a 65:35, by vol., ethyl ether/ethyl acetate mixture is added and the resulting mixture stirred for one hour and then filtered. The recovered crystals are washed with 65 ml. of 65:35, by vol., ethyl acetate/ethyl ether solution and dried under vacuum to give 41 g. of the pyridinium salt of 3-acetoxymethyl-7β-(thiophen-2-yl-acetamido)-ceph-2-em-4-carboxylic acid. This salt is added to a mixture of 650 ml. water and 650 ml. ethyl acetate and the mixture then acidified to pH 2 using 20% aqueous hydrochloric acid. The ethyl acetate layer is separated and the aqueous layer further extracted with 400 ml. ethyl acetate. The combined ethyl acetate extracts are washed twice with brine, dried over anhydrous sodium sulfate and the solvent then removed under reduced pressure to afford 34 g. of 3-acetoxymethyl-7β-(thiophen-2-yl-acetamido)-ceph-2-em-4-carboxylic acid.

PREPARATION 2

3-Hydroxymethyl-7β-(thiophen-2-yl-acetamido)-ceph-2-em-4-carboxylic acid

In this preparation 34 g. of 3-acetoxymethyl-7β-(thiophen-2-yl-cetamido)-ceph-2-em-4 phen-2-yl-acetamido-ceph-2-em-4carboxylic acid is added to a solution of 8.4 g. of lithium hydroxide monohydrate in 1000 ml. of water. The mixture is stirred at room temperature under nitrogen for 2 hours and then layered with 600 ml. of ethyl acetate. The pH of the mixture is then readjusted to pH 2 by the addition of 20% aqueous hydrochloric acid (~50 ml.). The ethyl acetate layer is separated and the aqueous layer is extracted twice with 500 ml. portions of ethyl acetate. The combined ethyl acetate extracts are washed twice with brine, dried over anhydrous sodium sulfate and evaporated to dryness under reduced pressure affording 24.2 g. of 3-hydroxymethyl-7β-(thiophen-2-yl-acetamido)-ceph-2-em-4-carboxylic acid.

PREPARATION 3

Benzhydryl 3-hydroxymethyl-7β-(thiophen-2-yl-acetamido)-ceph-2-em-4-carboxylate

In this preparation 24.2 g. of 3-hydroxymethyl-7β-(thiophen-2-yl-acetamido)-ceph-2-em-4-carboxylic acid is dissolved in 800 ml. of tetrahydrofuran, and then 15 g. of diphenyl diazomethane is added and the resulting mixture stirred at room temperature for 3 hours. The mixture is evaporated to dryness under reduced pressure and 250 ml. of 90:10, vol., ethyl ether/methylene chloride solution is added to the residue. After the mixture is stirred for 4 hours, the solid is recovered by filtration, and washed with 100 ml. of 90:10 ethyl ether/methyl chloride and then dried affording 28.5 g. of benzhydryl 3-hydroxymethyl-7β-(thiophen-2-yl-acetamido)-ceph-2-em-4-carboxylate.

PREPARATION 4

Benzhydryl 3-formyl-7β-(thiophen-2-yl-acetamido)-ceph-2-em-4-carboxylate

In this preparation 31 g. of dried chromium trioxide is added to a mixture of 51 g. of dried pyridine and 800 ml. of dry methylene chloride and stirred at 15° C under nitrogen for 20 minutes. 26 grams of benzhydryl 3-hydroxymethyl-7β-(thiophen-2-yl-acetamido)-ceph-2-em-4-carboxylate in 250 ml. of dry methylene chloride is added in one portion. The resulting mixture is stirred for 30 minutes and then filtered through diatomaceous earth. The contents of the reaction flask and the diatomaceous earth are washed with 500 ml. of methylene chloride and combined with the preceding filtrate and then washed with 400 ml. of 5% aqueous potassium hydroxide solution, 500 ml. of 20% aqueous hydrochloric acid and twice with 400 ml. brine. The aqueous washings are back extracted with 500 ml. of methylene chloride and the extracts added to the previously washed methylene chloride filtrate, and then dried over sodium sulfate and then stirred for 1 hour with 30 g. of silica gel. The mixture is filtered and the silica gel washed with 400 ml. 1:1 vol., ethyl acetate/methylene chloride. The combined filtrates are evaporated to dryness under reduced pressure and the resulting residue (26 g.) is recrystallized from ethyl ether/methylene chloride affording 21.4 g. of benzhydryl 3-formyl-7β-(thiophen-2-yl-acetamido)-ceph-2-em-4-carboxylate.

PREPARATION 5

Benzhydryl-3-(1-hydroxyprop-2-enyl)-7β-thiophen-2-yl-acetamido)-ceph-2-em-4-carboxylate In this preparation 2.5 g. of benzhydryl 3-formyl-7β-(thiophen-2-yl-acetamido)-ceph-2-em-4-carboxylate in 50 ml. of anhydrous tetrahydrofuran is stirred under nitrogen at −70° C and 10 ml. of a 2.5 molar solution of vinyl magnesium-chloride is added dropwise over 5 minutes. After 15 minutes, 50 ml. of pH 7-buffer solution of dibasic sodium phosphate and monobasic potassium phosphate is added to the well stirred mixture, and then warmed to room temperature. The mixture is diluted with 200 ml. of water and layered with 200 ml. of ethyl acetate. The pH of the aqueous layer is adjusted to pH 4 by the addition of 20% aqueous hydrochloric acid. The ethyl acetate layer is separated and the aqueous layer extracted with 100 ml. ethyl acetate. The ethyl acetate extracts are combined and then washed twice with 50 ml. portions of brine, dried over sodium sulfate and evaporated under reduced pressure affording benzhydryl 3-(1-hydroxyprop-2-enyl)-7β-(thiophen-2-yl-acetamido)-ceph-2-em-4-carboxylate as a pale yellow oil (2.7 g.).

The two isomers (α-hydroxy and β-hydroxy) are separated using thick-layer or column chromatography on silica gel using 45:5 vol./vol. of methylene chloride/acetone. They are then characterized by their nmr spectra (both oils).

Isomer 1 (higher Rf), nmr (CDCl$_3$) δ:3.78 (s, 2H); 4.596 (bd, J 14Hz, 1H); 4.9–5.7 (m, 6H); 6.366 (s, 1H); 6.7–7.5 (m, 14H);

Isomer 2 (lower Rf), nmr (CDCl$_3$) δ:3.79 (s, 2H); 4.63 (m, 1H); 5.0–5.8 (m, 6H); 6.25 (s, 1H); 6.8–7.5 (m 14H).

EXAMPLE 1

This example illustrates steps 1 and 2 of the process of the invention. In this example, 0.3 g. of benzhydryl 3-(1-hydroxyprop-2-enyl)-7β-(thiophen-2-ylacetamido)-ceph-2-em-4-carboxylate is dissolved in 3 ml. of methylene chloride at 0° C. and 5 ml. of methanol and 2 drops of 60% aqueous perchloric acid are added. The mixture is maintained at 0° C for 3 hours and then diluted with 10 ml. of ethyl acetate. The resulting solution is washed with water, dried and evaporated. The residue is chromatographed on a column of silica gel. Elution with a 1:25, by vol., mixture of acetone/methylene chloride affords two products. The first product is benzhydryl 3-(1-methoxyprop-2-enyl)-7β-(thiophen-2-ylacetamido)-ceph-2-em-4-carboxylate which is obtained as an oil. The second product, benzhydryl 3-(3-methoxyprop-1-(t)-enyl)-7β-(thiophen-2-ylacetamido)-ceph-2-em-4-carboxylate is obtained as an oil which crystallizes on standing; mp 148°–170° C; nmr (CDCl$_3$) δ: 3.24 (s, 3H); 3.81 (d, J 4Hz, 2H); 3.84 (s); 5.18 (d, J 4Hz, 1H); 5.25 (s, 1H); 5.53 (dd, J Hz, 1H) 5.70 (dt, J 16Hz, 5Hz, 1H); 6.12 (d, J 16Hz 1H); 6.45 (d, J 9Hz, 1H); 6.8–7.5 (m, 14H) ppm; Anal. Found; C, 64.26; H, 5.14; N, 4.79%. C$_{30}$H$_{28}$N$_2$O$_5$S$_2$ requires C, 64.27, H, 5.03, N, 5.00%.

The above obtained benzhydryl 3-(1-methoxyprop-2-enyl)-7β-(thiophen-2-ylacetamido)-ceph-2-em-4-carboxylate (0.12 g.) is dissolved in 5 ml. of methylene chloride and 5 ml. of methanol and 2 drops of 60% aqueous perchloric acid are added. The mixture left at room temperature for 48 hours and thereafter diluted with 10 ml. of ethyl acetate. The solution is washed twice with water, dried and evaporated to afford an oily residue. The residue is purified using thin-layer chromatography on silica gel. Elution with acetone:methylene chloride (1:20) yields benzhydryl 3-(3-methoxyprop-1-(t)-enyl)-7β-(thiophen-2-ylacetamido)-ceph-2-em-4-carboxylate.

Similarly, by following the above procedures, but replacing methanol with the alcohols listed in Table A, the corresponding compounds listed in Table B are prepared:

TABLE A ethanol
n-propanol
isopropanol
n-butanol
sec-butanol
tert-butanol
2-bromoethanol
2-chloroethanol
allyl alcohol
propargyl alcohol
cyclopentanol
benzyl alcohol

TABLE B benzhydryl 3-(3-ethoxyprop-1-(t)-enyl)-7β-(thiophen-2-yl-acetamido)-ceph-2-em-4-carboxylate, benzhydryl 3-(3-n-propoxyprop-1-(t)-enyl)-7β-(thiophen-2-ylacetamido)-ceph-2-em-4-carboxylate, benzhydryl 3-(3-isopropoxyprop-1-(t)-enyl)-7β-(thiophen-2-ylacetamido)-ceph-2-em-4-carboxylate, benzhydryl 3-(3-n-butoxyprop-1-(t)-enyl)-7β-(thiophen-2-ylacetamido)-ceph-2-em-4-carboxylate, benzhydryl 3-(3-sec-butoxyprop-1-(t)-enyl)-7β-(thiophen-2-ylacetamido)-ceph-2-em-4-carboxylate, benzhydryl 3-(3-tert-butoxyprop-1-(t)-enyl)-7β-(thiophen-2-ylacetamido)-ceph-2-em-4-carboxylate, benzhydryl 3-[3-(β-bromoethoxy)prop-1-(t)-enyl]-7β-(thiophen-2-ylacetamido)-ceph-2-em-4-carboxylate, benzhydryl 3-[3-(β-chloroethoxy)prop-1-(t)-enyl]-7β-(thiophen-2-ylacetamido-ceph-2-em-4-carboxylate, benzhydryl 3-(3-allyloxyprop-1-(t)-enyl)-7β-(thiophen-2-ylacetamido)-ceph-2-em-4-carboxylate, benzhydryl 3-(3-propargyloxyprop-1-(t)-enyl)-7β-(thiophen-2-ylacetamido)-ceph-2-em-4-carboxylate, benzhydryl 3-(3-cyclopentyloxyprop-1-(t)-enyl)-7β-(thiophen-2-ylacetamido)-ceph-2-em-4-carboxylate, and benzhydryl 3-(3-benzyloxyprop-1-(t)-enyl)-7β-(thiophen-2-ylacetamido)-ceph-2-em-4-carboxylate.

EXAMPLE 2

This example illustrates step 3 of the process of the invention. In this example 0.1 g. of benzhydryl 3-(3-methoxy prop-1-(t)-enyl)-7β-(thiophen-2-ylacetamido)-ceph-2-em-4-carboxylate is dissolved in 10 ml. of methylene chloride at 0° C. and about 30 mg. of m-chloroperbenzoic acid is added in 5 mg. aliquots over a period of three hours. The course of the reaction is monitored using thin-layer chromatography on silica gel and eluting with a 1:20, by vol., acetone/methylene chloride mixture. When less than 5% starting material remains, the reaction mixture is washed with aqueous sodium carbonate, dried and evaporated. The resulting residue is chromatographed on silica gel. Elution with a 1:20, by vol. acetone/methylene chloride mixture affords benzhydryl 3-(3-methoxyprop-1-(t)-enyl)-7β-(thiophen-2-ylacetamido)-ceph-3-em-4-carboxylate-1-oxide, mp 198°–202° C.

Similarly, by following the same procedure but using the products obtained in Example 1 as starting materials the following compounds are prepared:

benzhydryl 3-(3-ethoxyprop-1-(t)-enyl)-7β-(thiophen-2-ylacetamido)-ceph-3-em-4-carboxylate-1-oxide, benzhydryl 3-(3-n-propoxyprop-1-(t)-enyl)-7β-(thiophen-2-ylacetamido)-ceph-3-em-4-carboxylate-1-oxide, benzhydryl 3-(3-isopropoxyprop-1-(t)-enyl)-7β-(thiophen-2-ylacetamido)-ceph-3-em-4-carboxylate-1-oxide, benzhydryl 3-(3-n-butoxyprop-1-(t)-enyl)-7β-(thiophen-2-ylacetamido)-ceph-3-em-4-carboxylate-1-oxide, benzhydryl 3-(3-sec-butoxyprop-1-(t)-enyl)-7β-(thiophen-2-ylacetamido)-ceph-3-em-4-carboxylate-1-oxide, benzhydryl 3-(3-tert-butoxyprop-1-(t)-enyl)-7β-(thiophen-2-ylacetamido)-ceph-3-em-4-carboxylate-1-oxide, benzhydryl 3-[3-(β-bromoethoxy)prop-1-(t)-enyl]-7β-(thiophen-2-ylacetamido)-ceph-3-em-4-carboxylate-1-oxide, benzhydryl 3-[3-(β-chloroethoxy)prop-1-(t)-enyl]-7β-(thiophen-2-ylacetamido)-ceph-3-em-4-carboxylate-1-oxide, benzhydryl 3-(3-allyloxyprop-1-(t)-enyl-7β-(thiophen-2-ylacetamido)-ceph-3-em-4-carboxylate-1-oxide, benzhydryl 3-(3-propargyloxyprop-1-(t)-enyl)-7β-(thiophen-2-ylacetamido)-ceph-3-em-4-carboxylate-1-oxide, benzhydryl 3-(3-cyclopentyloxyprop-1-(t)-enyl)-7β-(thiophen-2-ylacetamido)-ceph-3-em-4-carboxylate-1-oxide, and benzhydryl 3-(3-benzyloxyprop-1-(t)-enyl)-7β-(thiophen-2-ylacetamido)-ceph-3-em-4-carboxylate-1-oxide.

EXAMPLE 3

This example illustrates step 4 of the process of the invention. In this example, a solution of 0.07 g. of benzhydryl 3-(3-methoxyprop-1-(t)-enyl)-7β-(thiophen-2-ylacetamido)-ceph-3-em-4-carboxylate-1-oxide in 5 ml. of dimethylformamide is stirred under nitrogen at 0° C and stannous chloride (0.08 g.) and acetyl chloride (0.15 ml.) are added. The mixture is stirred at 0° C for 15 minutes and then diluted with water and extracted with ethyl acetate. The combined ethyl acetate extracts are washed with water, dried over anhydrous sodium sulfate and evaporated. The residue is chromatographed on silica gel. Elution with a 1:20, by vol., mixture of acetone/methylene chloride affords benzhydryl 3-(3-methoxyprop-1-(t)-enyl)-7β-(thiophen-2-ylacetamido)-ceph-3-em-4-carboxylate, m.p. 140°–142° C.

Similarly, by following the same procedure but using the products obtained in Example 2 as starting materials, the following compounds are prepared:

benzhydryl 3-(3-ethoxyprop-1-(t)-enyl)-7β-(thiophen-2-ylacetamido)-ceph-3-em-4-carboxylate, benzhydryl 3-(3-n-propoxyprop-1-(t)-enyl)-7β-(thiophen-2-ylacetamido)-ceph-3-em-4-carboxylate, benzhydryl 3-(3-isopropoxyprop-1-(t)-enyl)-7β-(thiophen-2-ylacetamido)-ceph-3-em-4-carboxylate, benzhydryl 3-(3-n-butoxyprop-1-(t)-enyl)-7β-(thiophen-2-ylacetamido)-ceph-3-em-4-carboxylate, benzhydryl 3-(3-sec-butoxyprop-1-(t)-enyl)-7β-(thiophen-2-ylacetamido)-ceph-3-em-4-carboxylate, benzhydryl 3-(3-tert-butoxyprop-1-(t)-enyl)-7β-(thiophen-2-ylacetamido)-ceph-3-em-4-carboxylate, benzhydryl 3-[3-(β-bromoethoxy)prop-1-(t)-enyl]-7β-(thiophen-2-ylacetamido)-ceph-3-em-4-carboxylate, benzhydryl 3-[3-(β-chloroethoxy)prop-1-(t)-enyl]-7β-(thiophen-2-ylacetamido)-ceph-3-em-4-carboxylate, benzhydryl 3-(3-allyloxyprop-1-(t)-enyl)-7β-(thiophen-2-ylacetamido)-ceph-3-em-4-carboxylate, benzhydryl 3-(3-propargyloxyprop-1-(t)-enyl)-7β-(thiophen-2-ylacetamido)-ceph-3-em-4-carboxylate, benzhydryl 3-(3-cyclopentyloxyprop-1-(t)-enyl)-7β-(thiophen-2-ylacetamido)-ceph-3-em-4-carboxylate, and benzhydryl 3-(3-benzyloxyprop-1-(t)-enyl)-7β-(thiophen-2-ylacetamido)-ceph-3-em-4-carboxylate.

EXAMPLE 4

This example illustrates step 5 of the process of the invention. In this example, 5 ml. of trifluoroacetic acid is added to a stirring mixture of 0.05 g. of benzhydryl 3-(3-methoxyprop-1-(t)-enyl)-7β-(thiophen-2-ylacetamido)-ceph-3-em-4-carboxylate and 1 ml. of anisole at 0° C. Stirring is continued at 0° C for approximately 3 minutes. The mixture is then evaporated to drynss under reduced pressure. The resulting residue is dissolved in ethyl acetate and the ethyl acetate solution extracted with aqueous sodium bicarbonate. The aqueous extract is acidified with dilute hydrochloric acid and then extracted with ethyl acetate. The ethyl acetate extract is dried over sodium sulfate and evaporated to afford 3-(3-methoxyprop-1-(t)-enyl)-7β-(thiophen-2-ylacetamido)-ceph-3-em-4-carboxylic acid as a yellow solid.

The above obtained acid is dissolved in 0.5 ml of ethyl acetate and a saturated solution of sodium 2-ethylhexanoate in isopropanol is added until no further precipitate is formed. The collected solid is washed several times with isopropanol and then dried under vacuum to afford sodium 3-(3-methoxyprop-1-(t)-enyl)-7β-(thiophen-2-ylacetamido)-ceph-3-em-4-carboxylate; nmr ($D_6$-DMSO): 3.18 (s, 3H); 3.73 (s, 2H); 3.86 (d, J 7Hz, 2H); 4.96 (d, J 4Hz, 1H); 5.46 (dd, J 8Hz, 4Hz, 1H); 5.62 (dt, J 16Hz, 5Hz, 1H); 6.8–7.4 (m, 4H) ppm.

Similarly, by following the same procedure but using the products of Example 3 as starting materials, the following free acids and their pharmaceutically acceptable salts, including sodium salt, are prepared:

3-(3-ethoxyprop-1-(t)-enyl)-7β-(thiophen-2-ylacetamido)-ceph-3-em-4-carboxylic acid, 3-(3-n-propoxyprop-1-(t)-enyl)-7β-(thiophen-2-ylacetamido)-ceph-3-em-4-carboxylic acid, 3-(3-isopropoxyprop-1-(t)-enyl)-7β-(thiophen-2-ylacetamido)-ceph-3-em-4-carboxylic acid, 3-(3-n-butoxyprop-1-(t)-enyl)-7β-(thiophen-2-ylacetamido)-ceph-3-em-4-carboxylic acid, 3-(3-sec-butoxyprop-1-(t)-enyl)-7β-(thiophen-2-ylacetamido)-ceph-3-em-4-carboxylic acid,
3-(3-tert-butoxyprop-1-(t)-enyl)-7β-(thiophen-2-ylacetamido)-ceph-3-em-4-carboxylic acid,
3-[3-(β-bromoethoxy)prop-1-(t)-enyl]-7β-(thiophen-2-ylacetamido)-ceph-3-em-4-carboxylic acid,
3-[3-(β-chloroethoxy)prop-1-(t)-enyl]-7β-(thiophen-2-ylacetamido)-ceph-3-em-4-carboxylic acid,
3-(3-allyloxyprop-1-(t)-enyl)-7β-(thiophen-2-ylacetamido)-ceph-3-em-4-carboxylic acid,
3-(3-propargyloxyprop-1-(t)-enyl)-7β-(thiophen-2-ylacetamido)-ceph-3-em-4-carboxylic acid,
3-(3-cyclopentyloxyprop-1-(t)-enyl)-7β-(thiophen-2-ylacetamido)-ceph-3-em-4-carboxylic acid, and
3-(3-benzyloxyprop-1-(t)-enyl)-7β-(thiophen-2-ylacetamido)-ceph-3-em-4-carboxylic acid.

EXAMPLE 5

This example illustrates step 6 of the process of the invention. In this example 0.26 g. of benzhydryl 3-(3-methoxyprop-1-(t)-enyl)-7β-(thiophen-2-ylacetamido)-ceph-3-em -4-carboxylate is dissolved in 10 ml. of dichloromethane and 0.12 g. of phosphorus pentachloride and 0.05 ml. of pyridine are added. After stirring for three hours at room temperature, the solution is cooled to 0° C and 0.3 ml. of isobutyl alcohol is added and stirring is continued for one hour. Thereafter, 1 ml. of water is added and the mixture is stirred for 15 minutes. The mixture is then diluted with 10 ml. of dilute aqueous sodium bicarbonate solution and extracted twice with ethyl acetate. The combined extracts are washed with water and brine, dried over sodium sulfate, and evaporated under reduced pressure to afford benzhydryl 3-(3-methoxyprop-1-(t)-enyl)-7β-aminoceph-3-em-4-carboxylate.

Similarly, by following the same procedure but using the products of Example 3 as starting materials, the following compounds are prepared:
benzhydryl 3-(3-ethoxyprop-1-(t)-enyl)-7β-aminoceph-3-em-4-carboxylate,
benzhydryl 3-(3-n-propoxyprop-1-(t)-enyl)-7β-aminoceph-3-em-4-carboxylate,
benzhydryl 3-(isopropoxyprop-1-(t)-enyl)-7β-aminoceph-3-em-4-carboxylate,
benzhydryl 3-(3-n-butoxyprop-1-(t)-enyl)-7β-aminoceph-3-em-4-carboxylate,
benzhydryl 3-(3-sec-butoxyprop-1-(t)-enyl)-7β-aminoceph-3-em-4-carboxylate,
benzhydryl 3-(3-tert-butoxyprop-1-(t)-enyl)-7β-aminoceph-3-em-4-carboxylate,
benzhydryl 3-[3-(β-bromoethoxy)prop-1-(t)-enyl]-7β-aminoceph-3-em-4-carboxylate,
benzhydryl 3-[3-(β-chloroethoxy)prop-1-(t)-enyl]-7β-aminoceph-3-em-4-carboxylate,
benzhydryl 3-(3-allyloxyprop-1-(t)-enyl)-7β-aminoceph-3-em-4-carboxylate,
benzhydryl 3-(3-propargyloxyprop-1-(t)-enyl)-7β-aminoceph-3-em-4-carboxylate,
benzhydryl 3-(3-cyclopentyloxyprop-1-(t)-enyl)-7β-aminoceph-3-em-4-carboxylate, and
benzhydryl 3-(3-benzyloxyprop-1-(t)-enyl)-7β-aminoceph-3-em-4-carboxylate.

EXAMPLE 6

(A) This example illustrates step 7 of the process of the invention. In this example, 0.1 g. of benzhydryl 3-(3-methoxyprop-1-(t)-enyl)-7β-aminoceph-3-em-4-carboxylate is dissolved in 0.5 ml. of pyridine at 0° C and a solution of 0.1 g. of phenylacetyl chloride in 3 ml. of methylene chloride is added. After 20 minutes at 0° C, the mixture is diluted with 20 ml. of ethyl acetate and washed twice with water, dried over sodium sulfate and evaporated. The residue is purified using thick-layer chromatography. Elution with a 3.20, by vol., mixture of acetone/methylene chloride affords benzhydryl 3-(3-methoxyprop-1-(t)-enyl)-7β-phenylacetamido)-ceph-3-em-4-carboxylate.

(B) Similarly, by following the procedure recited in paragraph A above but replacing benzhydryl 3-(3-methoxyprop-1-(t)-enyl)-7β-aminoceph-3-em-4-carboxylate with other products of Example 5, the following compounds are produced:
benzhydryl 3-(3-ethoxyprop-1-(t)-enyl)-7β-(phenylacetamido)-ceph-3-em-4-carboxylate,
benzhydryl 3-(3-n-propoxyprop-1-(t)-enyl)-7β-(phenylacetamido)-ceph-3-em-4-carboxylate,
benzhydryl 3-(3-isopropoxyprop-1-(t)-enyl)-7β-phenylacetamido)-ceph-3-em-4-carboxylate,
benzhydryl 3-(3-n-butoxyprop-1-(t)-enyl)-7β-phenylacetamido)-ceph-3-em-4-carboxylate,
benzhydryl 3-(3-sec-butoxyprop-1-(t)-enyl)-7β-(phenylacetamido)-ceph-3-em-4-carboxylate,
benzhydryl 3-(3-tert-butoxyprop-1-(t)-enyl-7β-(phenylacetamido)-ceph-3-em-4-carboxylate,
benzhydryl 3-[3-(β-bromoethoxy)prop-1-(t)-enyl]-7β-(phenylacetamido)-ceph-3-em-4-carboxylate,
benzhydryl 3-[3-(β-chloroethoxy)prop-1-(t)-enyl]-7β-(phenylacetamido)-ceph-3-em-4-carboxylate,
benzhydryl 3-(3-allyloxyprop-1-(t)-enyl)-7β-(phenylacetamido)-ceph-3-em-4-carboxylate,
benzhydryl 3-(3-propargyloxyprop-1-(t)-enyl)-7β-(phenylacetamido)-ceph-3-em-4-carboxylate,
benzhydryl 3-(3-cyclopentyloxyprop-1-(t)-enyl)-7β-(phenylacetamido)-ceph-3-em-4-carboxylate, and
benzhydryl 3-(3-benzyloxyprop-1-(t)-enyl)-7β-(phenylacetamido)-ceph-3-em-4-carboxylate.

C) In like manner, by following the procedure recited in paragraph A above, but replacing phenylacetyl chloride with the reagents listed in Table C, hereinbelow, and using the products of Example 5, the compounds listed in Table D are prepared:

TABLE C

α-dichloroacetoxyphenylacetyl chloride
α-(tert-butoxycarbonyl)-α-phenylacetyl chloride
α-(tert-butoxycarbonylamino)-α-phenylacetyl chloride
α-(tert-butoxycarbonylamino)-α-(4-hydroxyphenyl)acetyl chloride
4-pyridylthioacetyl chloride
phenoxyacetyl chloride
trifluoromethylthioacetyl chloride
4-nitrophenylacetyl chloride
3-chlorophenylacetyl chloride
syn-2-methoxyimino(fur-2-yl)acetyl chloride

TABLE D benzhydryl 3-(3-methoxyprop-1-(t)-enyl)-7β[α-(dichloroacetoxy)-α-phenylacetamido]-ceph-3-em-4-carboxylate,
benzyhydryl 3-(3-ethoxyprop-1-(t)-enyl)-7β-[α-(dichloroacetoxy)-α-phenylacetamido]-ceph-3-em-4-carboxylate,
benzhydryl 3-(3-n-propoxyprop-1-(t)-enyl)-7β-[α-(dichloroacetoxy)-α-phenylacetamido]-ceph-3-em-4-carboxylate, benzhydryl 3-(3-isopropoxyprop-1-(t)-enyl)-7β-[α-(dichloroacetoxy)-α-phenylacetamido]ceph-3-em-4-carboxylate, benzhydryl 3-(3-n-butoxyprop-1-(t)-enyl)-7β-[α-(dichloroacetoxy)-α-phenylacetamido]-ceph-3-em-4-carboxylate, benzhydryl 3-(3-sec-butoxyprop-1-(t)-enyl)-7β-[α-(dichloroacetoxy)-α-phenylacetamido]-ceph-3-em-4-carboxylate, benzhydryl 3-(3-tert-butoxyprop-1-(t)-enyl)-7β-[α-(dichloroacetoxy)-α-phenylacetamidio]-ceph-3-em-4-carboxylate, benzhydryl 3-[3-(β-bromoethoxy)prop-1-(t)-enyl]-7β-[α-(dichloroacetoxy)-α-phenylacetamido]-ceph-3-em-4-carboxylate, benzyhydryl 3-[3-(β-chloroethoxy)prop-1-(t)-enyl]-7β-[α-(dichloroacetoxy)-α-phenylacetamido]-ceph-3-em-4-carboxylate, benzhydryl 3-(3-allyloxyprop-1-(t)-enyl)-7β-[α-(dichloroacetoxy)-α-phenylacetamido]-ceph-3-em-4-carboxylate, benzhydryl 3-(3-propargyloxyprop-1-(t)-enyl)-7β-[α-(dichloroacetoxy)-α-phenylacetamido]-ceph-3-em-4-carboxylate, benzyldryl 3-(3-cyclopentyloxyprop-1-(t)-enyl)-7β-[α-(dichloroacetoxy)-α-phenylacetamido]-ceph-3-em-4-carboxylate, benzhyhydryl 3-(3-benzyloxyprop-1-(t)-enyl)-7β[α-(dichloroacetoxy)-α-phenylacetamido]-ceph-3-em-4-carboxylate, benzhyhydryl 3-(3-methoxyprop-1-(t)-enyl)-7β-[α-(tert-butoxycarbonyl)-α-phenylacetamido]-ceph-3-em-4-carboxylate, benzhyhydryl 3-(3-ethoxyprop-1-(t)-enyl)-7β[α-(tert-butoxycarbonyl)-α-phenylacetamido]-ceph-3-em-4-carboxylate, benzhydryl 3-(3-n-propoxyprop-1-(t)-enyl)-7β[α-(tert-butoxycarbonyl)-α-phenylacetamido]-ceph-3-em-4-carboxylate, benzyhydryl 3-(3-isopropoxyprop-1-(t)-enyl)-7β-[α-(tert-butoxycarbonyl)-α-phenylacetamido]-ceph-3-em-4-carboxylate, benzhydryl 3-(3-n-butoxyprop-1-(t)-enyl)-7β[α-(tert-butoxycarbonyl)-α-phenylacetamido]-ceph-3-em-4-carboxylate, benzyhdryl 3-(3-sec-butoxyprop-1-(t)-enyl)-7β-[α(-tert-butoxycarbonyl)-α-phenylacetamido]-ceph-3-em-4-carboxylate, benzhydryl 3-(3-tert-butoxyprop-1-(t)-enyl)-7β-[α-(tert-butoxycarbonyl)-α-phenylacetamido]-ceph-3-em-4-carboxylate, benzyhydryl 3-[3-(β-bromoethoxy)prop-1-(t)-enyl]-7β-[α-(tert-butoxycarbonyl)-α-phenylacetamido]-ceph-3-em-4-carboxylate, benzhydryl 3-[3-(β-chloroethoxy)prop-1-(t)-enyl]-7β-[α(tert-butoxycarbonyl)-α-phenylacetamido]-ceph-3-em-4-carboxylate.

benzhydryl 3-(3-allyloxyprop-1-(t)-enyl)-7β[α-tert-butoxycarbonyl)-α-phenylacetamido]-ceph-3-em-4-carboxylate, benzhydryl 3-(3-propargyloxyprop-1-(t)-enyl)-7β-[α-(tert-butoxycarbonyl)-α-phenylacetamido]-ceph-3-em-4-carboxylate, benzhydryl 3-(3-cyclopentyloxyprop-1-(t)-enyl)-7β-[α-(tert-butoxycarbonyl)-α-phenylacetamido]-ceph-3-em-4-carboxylate, benzhydryl 3-(3-benzyloxyprop-1-(t)-enyl)-7β-[α-(tert-butoxycarbonyl)-α-phenylacetamido]-ceph-3-em-4-carboxylate, benzhydryl 3-(3-methoxyprop-1-(t)-enyl)-7β-[α-(tert-butoxycarbonylamino)-α-phenylacetamidio]-ceph-3-em-4-carboxylate, benzhydryl 3-(3-ethoxyprop-1-(t)-enyl)-7β-[α-(tert-butoxycarbonylamino)-α-phenylacetamido]-ceph-3-em-4-carboxylate, benzyhydryl 3-(3-n-propoxypro-1-(t)-enyl)-7β-[α-(tert-butoxycarbonylamino)-α-phenylacetamido]-ceph-3-em-4-carboxylate, benzhydryl 3-(3-isopropoxyprop-1-(t)-enyl)-7β-[α-(tert-butoxycarbonylamino)-α-phenylacetamido]-ceph-3-em-4-carboxylate, benzyhydryl 3-(3-n-butoxyprop-1-(t)-enyl)-7β-[α-(tert-butoxycarbonylamino)-α-phenylacetamido]-ceph-3-em-4-carboxylate, benzyhydryl 3-(3-sec-butoxyprop-1-(t)-enyl)-7β-[α-(tert-butoxycarbonylamino)-α-phenylacetamido]-ceph-3-em-4-carboxylate, benzhydryl 3-(3-tert-butoxyprop-1-(t)-enyl)-7β-[α-(tert-butoxycarbonylamino)-α-phenylacetamido]-ceph-3-em-4-carboxylate, benzhydryl 3-[3-(β-bromoethoxy)prop-1-(t)-enyl]-7β-[α-(tert-butoxycarbonylamino)-α-phenylacetamido]-ceph-3-em-4-carboxylate, benzhydryl 3-[3-(β-chloroethoxy)prop-1-(t)-enyl]-7β-[α-(tert-butoxycarbonylamino)-α-phenylacetamido]-ceph-3-em-4-carboxylate, benzhydryl 3-(3-allyloxyprop-1-(t)-enyl)-7β-[α-(tert-butoxycarbonylamino)-α-phenylacetamido]-ceph-3-em-4-carboxylate, benzhydryl 3-(3-propargyloxyprop-1-(t)-enyl)-7β-[α-(tert-butoxycarbonylamino)-α-phenylacetamido]-ceph-3-em-4-carboxylate, benzhydryl 3-(3-cyclopentyloxyprop-1-(t)-enyl)-7β-[α-(tert-butoxycarbonylamino)-α-phenylacetamido]-ceph-3-em-4-carboxylate, benzhydryl 3-(3-benzyloxyprop-1-(t)-enyl)-7β-[α-(tert-butoxycarbonylamino)-α-phenylacetamido]-ceph-3-em-4-carboxylate, benzyhydryl 3-(3-methoxyprop-1-(t)-enyl)-7β-[α-(tert-butoxycarbonylamino)-α-(4-hydroxyphenyl)acetamido]-ceph-3-em-4-carboxylate, benzhydryl 3-(3-ethoxyprop-1-(t)-enyl)-7β-[α-(tert-butoxycarbonylamino)-α-(4-hydroxyphenyl)acetamido]-ceph-3-em-4-carboxylate, benzhydryl 3-(3-n-propoxyprop-1-(t)-enyl)-7β-[α-(tert-butoxycarbonylamino)-α-(4-hydroxyphenyl)acetamido]-ceph-3-em-4-carboxylate, benzhydryl 3-(3-isopropoxyprop-1-(t)-enyl)-7β-[α-(tert-butoxycarbonylamino)-α-(4-hydroxyphenyl)acetamido]-ceph-3-em-4-carboxylate, benzhydryl 3-(3-n-butoxyprop-1-(t)-enyl)-7β-[α-(tert-butoxycarbonylamino)-α-(4-hydroxyphenyl)acetamido]-ceph-3-em-4-carboxylate, benzhydryl 3-(3-sec-butoxyprop-1-(t)-enyl)-7β-[α-(tert-butoxycarbonylamino)-α-(4-hydroxyphenyl)acetamido]-ceph-3-em-4-carboxylate, benzhydryl 3-(3-tert-butoxyprop-1-(t)-enyl)-7β-[α-(tert-butoxycarbonylamino)-α-(4-hydroxyphenyl)acetamido]-ceph-3-em-4-carboxylate, benzhydryl 3-[3-(β-bromoethoxy)prop-1-(t)-enyl]-7β-[α-(tert-butoxycarbonylamino)-α-(4-hydroxyphenyl)acetamido]-ceph3-em-4-carboxylate, benzhydryl 3-[3-(β-chloroethoxy)prop-1-(t)-enyl]-7β-[α-(tert-butoxycarbonylamino)-α-(4-hydroxyphenyl)acetamido]-ceph-3-em-4-carboxylate, benzhydryl 3-(3-allyloxyprop-1-(t)-enyl)-7β-[α-(tert-butoxycarbonylamino)-α-(4-hydroxyphenyl)acetamido]-ceph-3-em-4-carboxylate benzhydryl 3-(3-propargyloxyprop-1-(t)-enyl)-7β-[α-(tert-butoxycarbonylamino)-α-(4-hydroxyphenyl)acetamido]-ceph-3-em-4-carboxylate, benzhydryl 3-(3-cyclopentyloxyprop-1-(t)-enyl-7β-[α-(tert-butoxycarbonylamino)-α-(4-hydroxyphenyl)acetamido]-ceph-3-em-4-carboxylate, benzhydryl 3-(3-benzyloxyprop-1-(t)-enyl)-7β-[α-(tert-butoxycarbonylamino)-α-(4-hydroxyphenyl)acetamido]-ceph-3-em-4-carboxylate, benzhydryl 3-(3-methoxypropy-1-(t)-enyl)-7β-(4-pyridylthiocetamido)-ceph-3-em-4-carboxylate, benzhydryl 3-(3-ethoxypropy-1-(t)-enyl)-7β-(4-pyridylthioacetamido)-ceph-3-em-4-carboxylate, benzhydryl 3-(3-n-propoxyprop-1-(t)-enyl)-7β-(4-pyridylthioacetamido)-ceph-3-em-4-carboxylate, benzhydryl 3-(3-isopropoxyprop-1-(t)-enyl)-7β-(4-pyridylthioacetamido)-ceph-3-em-4-carboxylate, benzhydryl 3-(3-n-butoxyprop-1-(t)-enyl)-7β-(4-pyridylthioacetamido)-ceph-3-em-4-carboxylate, benzhydryl 3-(3-sec-butoxyprop-1-(t)-enyl)-7β-(4-pyridylthioacetamido)-ceph-3-em-4-carboxylate, benzhydryl 3-(3-tert-butoxyprop-1-(t)-enyl)-7β-(4-pyridylthioacetamido)-ceph-3-em-4-carboxylate, benzhydryl 3-[3-(β-bromoethoxy)prop-1-(t)-enyl]-7β-(4-pyridylthioacetamido)-ceph-3-em-4-carboxylate, benzhydryl 3-[3-(β-chloroethoxy)prop-1-(t)-enyl]-7β-(4)-pyridylthioacetamido)-ceph-3-em-4-carboxylate, benzhydryl 3-(3-allyloxyprop-1-(t)-enyl)-7β-(4-pyridylthioacetamido)-ceph-3-em-4-carboxylate, benzhydryl 3-(3-propargyloxyprop-1-(t)-enyl)-7β-(4-pyridylthioacetamido)-ceph-3-em-4-carboxylate, benzhydryl 3-(3-cyclopentyloxyprop-1-(t)-enyl)-7β-(4-pyridylthioacetamido)-ceph-3-em-4-carboxylate, benzhydryl 3-(3-benzyloxyprop-1-(t)-enyl)-7β-(4-pyridylthioacetamido)-ceph-3-em-4-carboxylate, benzhydryl 3-(3-methoxyprop-1-(t)-enyl)-7β-(phenoxyacetamido)-ceph-3-em-4-carboxylate, benzhydryl 3-(3-ethoxyprop-1-(t)-enyl)-7β-(phenoxyacetamido)-ceph-3-em-4-carboxylate, benzhydryl 3-(3-n-propoxyprop-1-(t)-enyl)-7β-(phenoxyacetamido)-ceph-3-em-4-carboxylate, benzhydryl 3-(3-isopropoxyprop-1-(t)-enyl)-7β-(phenoxyacetamido)-ceph-3-em-4-carboxylate, benzhydryl 3-(3-n-butoxyprop-1-(t)-enyl)-7β-(phenoxyacetamido)-ceph-3-em-4-carboxylate, benzhydryl 3-(3-sec-butoxyprop-1-(t)-enyl)-7β-(phenoxyacetamido)-ceph-3-em-4-carboxylate, benzhydryl 3-(3-tert-butoxyprop-1-(t)-enyl)-7β-(phenoxyacetamido)-ceph-3-em-4-carboxylate, benzhydryl 3-[3-(β-bromoethoxy)prop-1-(t)-enyl]-7β-(phenoxyacetamido)-ceph-3-em-4-carboxylate, benzhydryl 3-[3-(β-chloroethoxy)prop-1-(t)-enyl]-7β-(phenoxyacetamido)-ceph-3-em-4-carboxylate, benzhydryl 3-(3-allyloxyprop-1-(t)-enyl)-7β-(phenoxyacetamido)-ceph-3-em-4-carboxylate, benzhydryl 3-(3-propargyloxyprop-1-(t)-enyl)-7β-(phenoxyacetamido)-ceph-3-em-4-carboxylate, benzhydryl 3-(3-cyclopentyloxyprop-1-(t)-enyl)-7β-(phenoxyacetamido)-ceph-3-em-4-carboxylate, benzhydryl 3-(3-benzyloxyprop-1-(t)-enyl)-7β-(phenoxyacetamido)-ceph-3-em-4-carboxylate, benzhydryl 3-(3-methoxyprop-1-(t)-enyl)-7β-(trifluoromethylthioacetamido)-ceph-3-em-4-carboxylate, benzhydryl 3-(3-ethoxyprop-1-(t)-enyl)-7β-(trifluoromethylthioacetamido)-ceph-3-em-4-carboxylate, benzhydryl 3-(3-n-propoxyprop-1-(t)-enyl)-7β-(trifluoromethylthioacetamido)-ceph-3-em-4-carboxylate, benzhydryl 3-(3-isopropoxyprop-1-(t)-enyl)-7β-(trifluoromethylthioacetamido)-ceph-3-em-4-carboxylate, benzhydryl 3-(3-n-butoxyprop-1-(t)-enyl)-7β-(trifluoromethylthioacetamido)-ceph-3-em-4-carboxylate, benzhydryl 3-(3-sec-butoxyprop-1-(t)-enyl)-7β-(trifluoromethylthioacetamido)-ceph-3-em-4-carboxylate, benzhydryl 3-(3-tert-butoxyprop-1-(t)-enyl)-7β(trifluoromethylthioacetamido)-ceph-3-em-4-carboxylate, benzhydryl 3-[3-(β-bromoethoxy)prop-1-(t)-enyl]-7β-(trifluoromethylthioacetamido)-ceph-3-em-4-carboxylate, benzhydryl 3-[3-(β-chloroethoxy)prop-1-(t)-enyl]-7β-(trifluoromethylthioacetamido)-ceph-3-em-4-carboxylate, benzyhydryl 3-(3-allyloxyprop-1-(t)-enyl)-7β-(trifluoromethylthioacetamido)-ceph-3-em-4-carboxylate, benzhydryl 3-(3-propargyloxyprop-1-(t)-enyl)-7β-(trifluoromethylthioacetamido)-ceph-3-em-4-carboxylate, benzhydryl 3-(3-cyclopentyloxyprop-1-(t)-enyl)-7β-(trifluoromethylthioacetamido)-ceph-3-em-4-carboxylate, benzhydryl 3-(3-benzyloxyprop-1-(t)-enyl)-7β-(trifluoromethylthioacetamido)-ceph-3-em-4-carboxylate, benzhydryl 3-(3-methoxyprop-1-(t)-enyl)-7β-(4-nitrophenylacetamido)-ceph-3-em-4-carboxylate, benzhydryl 3-(3-ethoxyprop-1-(t)-enyl)-7β-(4-nitrophenylacetamido)-ceph-3-em-4-carboxylate, benzhydryl 3-(3-n-propoxyprop-1-(t)-enyl)-7β-(4-nitrophenylacetamido)-ceph-3-em-4-carboxylate, benzhydryl 3-(3-isopropoxyprop-1-(t)-enyl)-7β-(4-nitrophenylacetamido)-ceph-3-em-4-carboxylate, benzhydryl 3-(3-n-butoxyprop-1-(t)-enyl)-7β-(4-nitrophenylacetamido)-ceph-3-em-4-carboxylate, benzhydryl 3-(3-sec-butoxyprop-1-(t)-enyl)-7β-(4-nitrophenylacetamido)-ceph-3-em-4-carboxylate, benzhydryl 3-(3-tert-butoxyprop-1-(t)-enyl)-7β-(4-nitrophenylacetamido)-ceph-3-em-4-carboxylate, benzhydryl 3-[3-(β-bromoethoxy)prop-1-(t)-enyl]-7β-(4-nitrophenylacetamido)-ceph-3-em-4-carboxylate, benzhydryl 3-[3-(β-chloroethoxy)prop-1-(t)-enyl]-7β(4-nitrophenylacetamido)-ceph-3-em-4-carboxylate, benzhydryl 3-(3-allyloxyprop-1-(t)-enyl)-7β-(4-nitrophenylacetamido)-ceph-3-em-4-carboxylate, benzhydryl 3-(3-propargyloxyprop-1-(t)-enyl)-7β-(4-nitrophenylacetamido)-ceph-3-em-4-carboxylate, benzhydryl 3-(3-cyclopentyloxyprop-1-(t)-enyl)-7β-(4-nitrophenylacetamido)-ceph-3-em-4-carboxylate, benzhydryl 3-(3-benzyloxyprop-1-(t)-enyl)-7β-(4-nitrophenylacetamido)-ceph-3-em-4-carboxylate, benzhydryl 3-(3-methoxyprop-1-(t)-enyl)-7β-(3-chlorophenylacetamido)-ceph-3-em-4-carboxylate, benzhydryl 3-(3-ethoxyprop-1-(t)-enyl)-7β-(3-chlorophenylacetamido)-ceph-3-em-4-carboxylate, benzhydryl 3-(3-n-propoxyprop-1-(t)-enyl)-7β-(3-chlorophenylacetamido)-ceph-3-em-4-carboxylate, benzhydryl 3-(3-isopropoxyprop-1-(t)-enyl)-7β(3-chlorophenylcetamido)-ceph-3-em-4-carboxylate, benzhydryl 3-(3-n-butoxyprop-1-(t)-enyl)-7β-(3-chlorophenylacetamido)-ceph-3-em-4-carboxylate, benzhydryl 3-(3-sec-butoxyprop-1-(t)-enyl)-7β-(3-chlorophenylacetamido)-ceph-3-em-4-carboxylate, benzhydryl 3-(3-tert-butoxyprop-1-(t)-enyl)-7β(3-chlorophenylacetamido)-ceph-3-em-4-carboxylate, benzhydryl 3-[3-(β-bromoethoxy)prop-1-(t)-enyl]-7β-(3-chlorophenylacetamido)-ceph-3-em-4-carboxylate, benzhydryl 3-[3-(β-chloroethoxy)prop-1-(t)-enyl]-7β-(3-chlorophenylacetamido)-ceph-3-em-4-carboxylate, benzhydryl 3-(3-allyloxyprop-1-(t)-enyl)-7β-(3-chlorophenylacetamido)-ceph-3-em-4-carboxylate, benzhydryl 3-(3-propargyloxyprop-1-(t)-enyl)-7β-(3-chlorophenylacetamido)-ceph-3-em-4-carboxylate, benzhydryl 3-(3-cyclopentyloxyprop-1-(t)-enyl)-7β-(3-chlorophenylacetamido)-ceph-3-em-4-carboxylate, benzhydryl 3-(3-benzyloxyprop-1-(t)-enyl)-7β-(3-chlorophenylacetamido)-ceph-3-em-4-carboxylate, benzhydryl 3-(3-methoxyprop-1-(t)-enyl)-7β-[2-methoxyimino-2-(fur-2-yl)acetamido]-ceph-3-em-4-carboxylate, benzhydryl 3-(3-ethoxyprop-1-(t)-enyl)-7β-[2-methoxyimino-2-(fur-2-yl)acetamido]-ceph-3-em-4-carboxylate, benzhydryl 3-(3-n-propoxyprop-1-(t)-enyl)-7β-[2-methoxyimino-2-(fur-2-yl)acetamido]-ceph-3-em-4-carboxylate, benzhydryl 3-(3-isopropoxyprop-1-(t)-enyl)-7β-[2-methoxyimino-2-(fur-2-yl)acetamido]-ceph-3-em-4-carboxylate, benzhydryl 3-(3-n-butoxyprop-1-(t)-enyl)-7β-[2-methoxyimino-2-(fur-2-yl)acetamido]-ceph-3-em-4-carboxylate, benzhydryl 3-(3-sec-butoxyprop-1-(t)-enyl)-7β-[2-methoxyimino-2-(fur-2-yl)acetamido]-ceph-3-em-4-carboxylate, benzhydryl 3-(3-tert-butoxyprop-1-(t)-enyl)-7β-[2-methoxyimino-2-(fur-2-yl)acetamido]-ceph-3-em-4-carboxylate, benzhydryl 3-[3-(β-bromoethoxy)prop-1-(t)-enyl]-7β-[2-methoxyimino-2-(fur-2-yl)acetamido]-ceph-3-em-4-carboxylate, benzhydryl 3-[3-(β-chloroethoxy)prop-1-(t)-enyl]-7β-[2-methoxyimino-2-(fur-2-yl)acetamido]-ceph-3-em-4-carboxylate, benzhydryl 3-(3allyloxyprop-1-(t)-enyl)-7β-[2-methoxyimino-2-(fur-2-yl)acetamido]ceph-3-em-4-carboxylate, benzhydryl 3-(3-propargyloxyprop-1-(t)-enyl)-7β-[2-methoxyimino-2-(fur-2-yl)acetamido]-ceph-3-em-4-carboxylate, benzhydryl 3-(3-cyclopentyloxyprop-1-(t)-enyl)-7β-[2-methoxyimino-2-(fur-2-yl)acetamido]-ceph-3-em-4-carboxylate, and benzhydryl 3-(3-benzyloxyprop-1-(t)-enyl)-7β-[2-methoxyimino-2-(fur-2-yl)acetamido]-ceph-3-em-4-carboxylate.

EXAMPLE 7

This example illustrates step 7 of the process of the invention. In this example 0.1 g. of benzhydryl 3-(3-methoxyprop-1-(t)-enyl)-7β-aminoceph-3-em-4-carboxylate is dissolved in 1 ml. of methylene chloride and 1 ml. of ethyl acetate, and 0.12 g. of 1H-tetrazol-1-ylacetic acid and 0.15 g. of dicyclohexylcarbodiimide are added. After stirring for one hour at room temperature, a solution of 0.07 g. of oxalic acid in 2 ml. of methanol is added. The mixture is then stirred for 10 minutes and then diluted with 10 ml. of ethyl acetate. The resulting solution is washed with dilute aqueous sodium bicarbonate solution and then dried over anhydrous sodium sulfate and evaporated. The residue is purified using thick-layer chromatography. Elution with a 1:4, by vol., mixture of acetone/methylene chloride affords benzhydryl 3-(3-methoxyprop-1-(t)-enyl)-7β-(1H-tetrazol-1-ylacetamido)-ceph-3-em-4-carboxylate.

Similarly, by following the same procedure, but replacing benzhydryl 3-(3-methoxyprop-1-(t)-enyl)-7β-aminoceph-3-em-4-carboxylate with the products of Example 5, the following compounds are prepared:

benzhydryl 3-(3-ethoxyprop-1-(t)-enyl)-7β-(1H-tetrazol-1-ylacetamido)-ceph-3-em-4-carboxylte, benzhydryl 3-(3-n-propoxyprop-1-(t)-enyl)-7β-(1H-tetrazol-1-ylacetamido)-ceph-3-em-4-carboxylate, benzhydryl 3-(3-isopropoxyprop-1-(t)-enyl)-7β-(1H-tetrazol-1-ylacetamido)-ceph-3-em-4-carboxylate, benzhydryl 3-(3-n-butoxyprop-1-(t)-enyl)-7β-(1H-tetrazol-1-ylacetamido)-ceph-3-em-4-carboxylate,.

benzhydryl 3-(3-sec-butoxyprop-1-(t)-enyl)-7β-(1H-tetrazol-1-ylacetamido)-ceph-3-em-4-carboxylate, benzhydryl 3-(3-tert-butoxyprop-1-(t)-enyl)7β-(1H-tetrazol-1-ylacetamido)-ceph-3-em-4-carboxylate, benzhydryl 3-[3-(β-bromoethoxy)prop-1-(t)-enyl]-7β-(1H-tetrazol-1-ylacetamido)-ceph-3-em-4-carboxylate, benzhydryl 3-[3-(β-chloroethoxy)prop-1-(t)-enyl]-7β-(1H-tetrazol-1-ylacetamido)-ceph-3-em-4-carboxylate, benzhydryl 3-(3-allyloxyprop-1-(t)-enyl)-7β-(1H-tetrazol-1-ylacetamido)-ceph-3-em-4-carboxylate, benzhydryl 3-(3-proparglyoxyprop-1-(t)-enyl)-7β-(1H-tetrazol-1-ylacetamido)-ceph-3-em-4-carboxylate, benzhydryl 3-(3-cyclopentyloxyprop-1-(t)-enyl)-7β-(1H-tetrazol-1-ylacetamido)-ceph-3-em-4-carboxylate, and benzhydryl 3-(3-benzyloxyprop-1-(t)-enyl)-7β-(1H-tetrazol-1-ylacetamido)-ceph-3-em-4-carboxylate.

EXAMPLE 8

This example illustrates step 8 of the process of the invention. In this example, 5 ml. of trifluoroacetic acid is added to a stirring mixture of 0.2 g. of benzhydryl 3-(3-methoxyprop-1-(t)-enyl)-7β-(phenylacetamido)-ceph-3-em-4-carboxylate and 1 ml. of anisole at 0° C. Stirring is continued at 0° C for approximately 2 minutes. Thereafter the mixture is evaporated to dryness under reduced pressure to afford 3-(3-methoxyprop-1-(t)-enyl)-7β-(phenylacetamido)-ceph-3-em-4-carboxylic acid.

The above obtained acid is dissolved in tetrahydrofuran, filtered and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum to afford sodium 3-(3-methoxyprop-1-(t)-enyl)-7β-(phenylacetamido)-ceph-3-em-4-carboxylate.

Similarly, by following the same procedure using the products of Examples 6 and 7 wherein the 7β-substituent is phenylacetamido, 4-pyridylthioacetamido, phenoxyacetamido, trifluoromethylthioacetamido, 4-nitrophenylacetamido, 3-chlorophenylacetamido, 2-methoxyimino-2-(fur-2-yl)acetamido or 1H-tetrazol-1-ylacetamido, the following free acids and their pharmaceutically acceptable salts, including sodium salts, are prepared:

3-(3-ethoxyprop-1-(t)-enyl)-7β-(phenylacetamido)-ceph-3-em-4-carboxylic acid,
3-(3-n-propoxyprop-1-(t)-enyl)-7β-(phenylacetamido)-ceph-3-em-4-carboxylic acid,
3-(3-isopropoxyprop-1-(t)-enyl)-7β-(phenylacetamido)-ceph-3-em-4-carboxylic acid,
3-(3-n-butoxyprop-1-(t)-enyl)-7β-(phenylacetamido)-ceph-3-em-4-carboxylic acid,
3-(3-sec-butoxyprop-1-(t)-enyl)-7β-(phenylacetamido)-ceph-3-em-4-carboxylic acid,
3-(3-tert-butoxyprop-1-(t)-enyl)-7β-(phenylacetamido)-ceph-3-em-4-carboxylic acid,
3-[3-(β-bromoethoxy)prop-1-(t)-enyl]-7β-(phenylacetamido)-ceph-3-em-4-carboxylic acid,
3-[3-(β-chloroethoxy)prop-1-(t)-enyl]-7β-(phenylacetamido)-ceph-3-em-4-carboxylic acid,
3-(3-allyloxyprop-1-(t)-enyl)-7β-(phenylacetamido)-ceph-3-em-4-carboxylic acid,
3-(3-propargyloxyprop-1-(t)-enyl)-7β-(phenylacetamido)-ceph-3-em-4-carboxylic acid,
3-(3-cyclopentyloxyprop-1-(t)-enyl)-7β-(phenylacetamido)-ceph-3-em-4-carboxylic acid,
3-(3-benzyloxyprop-1-(t)-enyl)-7β-(phenylacetamido)-ceph-3-em-4-carboxylic acid,
3-(3-methoxyprop-1-(t)-enyl)-7β-(4-pyridylthioacetamido)-ceph-3-em-4-carboxylic acid,
3-(3-ethoxyprop-1-(t)-enyl)-7β-(4-pyridylthioacetamido)-ceph-3-em-4-carboxylic acid,
3-(3-n-propoxyprop-1-(t)-enyl)-7β-(4-pyridylthioacetamido)-ceph-3-em-4-carboxylic acid,
3-(3-isopropoxyprop-1-(t)-enyl)-7β-(4-pyridylthioacetamido)-ceph-3-em-4-carboxylic acid,
3-(3-n-butoxyprop-1-(t)-enyl)-7β-(4-pyridylthioacetamido)-ceph-3-em-4-carboxylic acid,
3-(3-sec-butoxyprop-1-(t)-enyl)-7β-(4-pyridylthioacetamido)-ceph-3-em-4-carboxylic acid,
3-(3-tert-butoxyprop-1-(t)-enyl)-7β-(4-pyridylthioacetamido)-ceph-3-em-4-carboxylic acid,
3-[3-(β-bromoethoxy)prop-1-(t)-enyl]-7β-(4-pyridylthioacetamido)-ceph-3-em-4-carboxylic acid,
3-[3-(β-chloroethoxy)prop-1-(t)-enyl]-7β-(4-pyridylthioacetamido)-ceph-3-em-4-carboxylic acid,
3-(3-allyloxyprop-1-(t)-enyl)-7β-(4-pyridylthioacetamido)-ceph-3-em-4-carboxylic acid,
3-(3-propargyloxyprop-1-(t)-enyl)-7β-(4-pyridylthioacetamido)-ceph-3-em-4-carboxylic acid,
3-(3-cyclopentyloxyprop-1-(t)-enyl)-7β-(4-pyridylthioacetamido)-ceph-3-em-4-carboxylic acid,
3-(3-benzyloxyprop-1-(t)-enyl)-7β-(4-pyridylthioacetamido)-ceph-3-em-4-carboxylic acid,
3-(3-methoxyprop-1-(t)-enyl)-7β-(phenoxyacetamido)-ceph-3-em-4-carboxylic acid,
3-(3-ethoxyprop-1-(t)-enyl)-7β-(phenoxyacetamido)-ceph-3-em-4-carboxylic acid,
3-(3-n-propoxyprop-1-(t)-enyl)-7β-(phenoxyacetamido)-ceph-3-em-4-carboxylic acid,
3-(3-isopropoxyprop-1-(t)-enyl)-7β-(phenoxyacetamido)-ceph-3-em-4-carboxylic acid,
3-(3-n-butoxyprop-1-(t)-enyl)-7β-(phenoxyacetamido)-ceph-3-em-4-carboxylic acid,
3-(3-sec-butoxyprop-1-(t)-enyl)-7β-(phenoxyacetamido)-ceph-3-em-4-carboxylic acid,
3-(3-tert-butoxyprop-1-(t)-enyl)-7β-(phenoxyacetamido)-ceph-3-em-4-carboxylic acid,
3-[3-(β-bromoethoxy)prop-1-(t)-enyl]-7β-(phenoxyacetamido)-ceph-3-em-4-carboxylic acid,
3-[3-(β-chloroethoxy)prop-1-(t)-enyl]-7β-(phenoxyacetamido)-ceph-3-em-4-carboxylic acid,
3-(3-allyloxyprop-1-(t)-enyl)-7β-(phenoxyacetamido)-ceph-3-em-4-carboxylic acid,
3-(3-propargyloxyprop-1-(t)-enyl)-7β-(phenoxyacetamido)-ceph-3-em-4-carboxylic acid,
3-(3-cyclopentyloxyprop-1-(t)-enyl)-7β-(phenoxyacetamido)-ceph-3-em-4-carboxylic acid,
3-(3-benzyloxyprop-1-(t)-enyl)-7β-(phenoxyacetamido-ceph-3-em-4-carboxylic acid,
3-(3-methoxyprop-1-(t)-enyl)-7β-(trifluoromethylthioacetamido)-ceph-3-em-4-carboxylic acid,
3-(3-ethoxyprop-1-(t)-enyl)-7β-(trifluoromethylthioacetamido)-ceph-3-em-4-carboxylic acid,
3-(3-n-propoxyprop-1-(t)-enyl)-7β-(trifluoromethylthioacetamido)-ceph-3-em-4-carboxylic acid,
3-(3-isopropoxyprop-1-(t)-enyl)-7β-(trifluoromethylthioacetamido)-ceph-3-em-4-carboxylic acid,
3-(3-n-butoxyprop-1-(t)-enyl)-7β-(trifluoromethylthioacetamido)-ceph-3-em-4-carboxylic acid,
3-(3-sec-butoxyprop-1-(t)-enyl)-7β-(trifluoromethylthioacetamido)-ceph-3-em-4-carboxylic acid,
3-(3-tert-butoxyprop-1-(t)-enyl)-7β-(trifluoromethylthioacetamido)-ceph-3-em-4-carboxylic acid,
3-[3-(β-bromoethoxy)prop-1-(t)-enyl]-7β-(trifluoromethylthioacetamido)-ceph-3-em-4-carboxylic acid,
3-[3-(β-chloroethoxy)prop-1-(t)-enyl]-7β-(trifluoromethylthioacetamido)-ceph-3-em-4-carboxylic acid,
3-(3-allyloxyprop-1-(t)-enyl)-7β-(trifluoromethylthioacetamido)-ceph-3-em-4-carboxylic acid,
3-(3-propargyloxyprop-1-(t)-enyl)-7β-(trifluoromethylthioacetamido)-ceph-3-em-4-carboxylic acid,
3-(3-cyclopentyloxyprop-1-(t)-enyl)-7β-(trifluoromethylthioacetamido)-ceph-3-em-4-carboxylic acid,
3-(3-benzyloxyprop-1-(t)-enyl)-7β-(trifluoromethylthioacetamido)-ceph-3-em-4-carboxylic acid,
3-(3-methoxyprop-1-(t)-enyl)-7β-(4-nitrophenylacetamido)-ceph-3-em-4-carboxylic acid,
3-(3-ethoxyprop-1-(t)-enyl)-7β-(4-nitrophenylacetamido)-ceph-3-em-4-carboxylic acid,
3-(3-n-propoxyprop-1-(t)-enyl)-7β-(4-nitrophenylacetamido)-ceph-3-em-4-carboxylic acid,
3-(3-isopropoxyprop-1-(t)-enyl)-7β-(4-nitrophenylacetamido)-ceph-3-em-4-carboxylic acid,
3-(3-n-butoxyprop-1-(t)-enyl)-7β-(4-nitrophenylacetamido)-ceph-3-em-4-carboxylic acid,
3-(3-sec-butoxyprop-1-(t)-enyl)-7β-(4-nitrophenylacetamido)-ceph-3-em-4-carboxylic acid,
3-(3-tert-butoxyprop-1-(t)-enyl)-7β-(4-nitrophenylacetamido)-ceph-3-em-4-carboxylic acid,
3-[3-(β-bromoethoxy)prop-1-(t)-enyl]-7β-(4-nitrophenylacetamido)-ceph-3-em-4-carboxylic acid,
3-[3-(β-chloroethoxy)prop-1-(t)-enyl]-7β-(4-nitrophenylacetamido)-ceph-3-em-4-carboxylic acid,
3-(3-allyloxyprop-1-(t)-enyl)-7β-(4-nitrophenylacetamido)-ceph-3-em-4-carboxylic acid,
3-(3-propargyloxyprop-1-(t)-enyl)-7β-(4-nitrophenylacetamido)-ceph-3-em-4-carboxylic acid,
3-(3-cyclopentyloxyprop-1-(t)-enyl)-7β-(4-nitrophenylacetamido)-ceph-3-em-4-carboxylic acid,
3-(3-benzyloxyprop-1-(t)-enyl)-7β-(4-nitrophenylacetamido)-ceph-3-em-4-carboxylic acid,
3-(3-methoxyprop-1-(t)-enyl)-7β-(3-chlorophenylacetamido)-ceph-3-em-4-carboxylic acid,
3-(3-ethoxyprop-1-(t)-enyl)-7β-(3-chlorophenylacetamido)-ceph-3-em-4-carboxylic acid,
3-(3-n-propoxyprop-1-(t)-enyl)-7β-(3-chlorophenylacetamido)-ceph-3-em-4-carboxylic acid, 3-(3-isopropoxyprop-1-(t)-enyl)-7β-(3-chloro-phenylacetamido)-ceph-3-em-4-carboxylic acid, 3-(3-n-butoxyprop-1-(t)-enyl)-7β-(3-chloro-phenylacetamido)-ceph-3-em-4-carboxylic acid, 3-(3-sec-butoxyprop-1-(t)-enyl)-7β-(3-chloro-phenylacetamido)-ceph-3-em-4-carboxylic acid, 3-(3-tert-butoxyprop-1-(t)-enyl)-7β-(3-chloro-phenylacetamido)-ceph-3-em-4-carboxylic acid, 3-[3-(β-bromoethoxy)prop-1-(t)-enyl]-7β-(3-chloro-phenylacetamido)-ceph-3-em-4-carboxylic acid, 3-[3-(β-chloroethoxy)prop-1-(t)-enyl]-7β-(3-chloro-phenylacetamido)-ceph-3-em-4-carboxylic acid, 3-(3-allyloxyprop-1-(t)-enyl)-7β-(3-chloro-phenylacetamido)-ceph-3-em-4-carboxylic acid, 3-(3-propargyloxyprop-1-(t)-enyl)-7β-(3-chloro-phenylacetamido)-ceph-3-em-4-carboxylic acid, 3-(3-cyclopentyloxyprop-1-(t)-enyl)-7β-(3-chloro-phenylacetamido)-ceph-3-em-4-carboxylic acid, 3-(3-benzyloxyprop-1-(t)-enyl)-7β-(3-chloro-phenylacetamido)-ceph-3-em-4-carboxylic acid, 3-(3-methoxyprop-1-(t)-enyl)-7β-[2-methoxyimino-2-(fur-2-yl)acetamido]-ceph-3-em-4-carboxylic acid (syn-isomer), 3-(3-ethoxyprop-1-(t)-enyl)-7β-[2-methoxyimino-2-(fur-2-yl)acetamido]-ceph-3-em-4-carboxylic acid (syn-isomer), 3-(3-n-propoxyprop-1-(t)-enyl)-7β-[2-methoxyimino-2-(fur-2-yl)acetamido]-ceph-3-em-4-carboxylic acid (syn-isomer), 3-(3-isopropoxyprop-1-(t)-enyl)-7β-[2-methoxyimino-2-(fur-2-yl)acetamido]-ceph-3-em-4-carboxylic acid (syn isomer), 3-(3-n-butoxyprop-1-(t)-enyl)-7β-[2-methoxyimino-2-(fur-2-yl)acetamido]-ceph-3-em-4-carboxylic acid (syn-isomer), 3-(3-sec-butoxyprop-1-(t)-enyl)-7β-[2-methoxyimino-2-(fur-2-yl)acetamido]-ceph-3-em-4-carboxylic acid (syn-isomer), 3-(3-tert-butoxyprop-1-(t)-enyl)-7β-[2-methoxyimino-2-(fur-2-yl)acetamido]-ceph-3-em-4-carboxylic acid (syn-isomer), 3-[3-(β-bromoethoxy)prop-1-(t)-enyl]-7β-[2-methoxyimino-2-(fur-2-yl)acetamido]-ceph-3-em-4-carboxylic acid (syn-isomer), 3-[3-(β-chloroethoxy)prop-1-(t)-enyl]-7β-[2-methoxyimino-2-(fur-2-yl)acetamido]-ceph-3-em-4-carboxylic acid (syn-isomer), 3-(3-allyloxyprop-1-(t)-enyl)-7β-[2-methoxyimino-2-(fur-2-yl)acetamido]-ceph-3-em-4-carboxylic acid (syn-isomer), 3-(3-propargyloxyprop-1-(t)-enyl)-7β-[2-methoxyimino-2-(fur-2-yl)acetamido]-ceph-3-em-4-carboxylic acid (syn-isomer), 3-(3-cyclopentyloxyprop-1-(t)-enyl)-7β-[2-methoxyimino-2-(fur-2-yl)acetamido]-ceph-3-em-4-carboxylic acid (syn-isomer), 3-(3-benzyloxyprop-1-(t)-enyl)-7β-[2-methoxyimino-2-(fur-2-yl)acetamido]-ceph-3-em-4-carboxylic acid (syn-isomer), 3-(3-methoxyprop-1-(t)-enyl)-7β-(1H-tetrazol-1-ylacetamido)-ceph-3-em-4-carboxylic acid, 3-(3-ethoxyprop-1-(t)-enyl)-7β-(1H-tetrazol-1-ylacetamido)-ceph-3-em-4-carboxylic acid, 3-(3-n-propoxyprop-1-(t)-enyl)-7β-(1H-tetrazol-1-ylacetamido)-ceph-3-em-4-carboxylic acid, 3-(3-isopropoxyprop-1-(t)-enyl)-7β-(1H-tetrazol-1-ylacetamido)-ceph-3-em-4-carboxylic acid, 3-(3-n-butoxyprop-1-(t)-enyl)-7β-(1H-tetrazol-1-ylacetamido)-ceph-3-em-4-carboxylic acid, 3-(3-sec-butoxyprop-1-(t)-enyl)-7β-(1H-tetrazol-1-ylacetamido)-ceph-3-em-4-carboxylic acid, 3-(3-tert-butoxyprop-1-(t)-enyl)-7β-(1H-tetrazol-1-ylacetamido)-ceph-3-em-4-carboxylic acid, 3-[3-(β-bromoethoxy)prop-1-(t)-enyl]-7β-(1H-tetrazol-1-ylacetamido)-ceph-3-em-4-carboxylic acid, 3-[3-(β-chloroethoxy)prop-1-(t)-enyl]-7β-(1H-tetrazol-1-ylacetamido)-ceph-3-em-4-carboxylic acid, 3-(3-allyloxyprop-1-(t)-enyl)-7β-(1H-tetrazol-1-ylacetamido)-ceph-3-em-4-carboxylic acid, 3-(3-propargyloxyprop-1-(t)-enyl)-7β-(1H-tetrazol-1-ylacetamido)-ceph-3-em-4-carboxylic acid, 3-(3-cyclopentyloxyprop-1-(t)-enyl)-7β-(1H-tetrazol-1-ylacetamido)-ceph-3-em-4-carboxylic acid, and 3-(3-benzyloxyprop-1-(t)-enyl)-7β-(1H-tetrazol-1-ylacetamido)-ceph-3-em-4-carboxylic acid.

EXAMPLE 9

This example illustrates step 8 of the process of the invention. In this example, 0.2 g. of benzhydryl 3-(3-methoxyprop-1-(t)-enyl)-7β-[α-(tert-butoxycarbonyl)-α-phenylacetamido]-ceph-3-em-4-carboxylate in 1 ml. of anisole and 6 ml. of trifluoroacetic acid is stirred at 0° C for 30 minutes. Thereafter, the solvents are removed under reduced pressure and the resulting residue is washed twice with 0.5 ml. portions of ether to afford 3-(3-methoxyprop-1-(t)-enyl)-7β-(α-carboxy-α-phenylacetamido)-ceph-3-em-4-carboxylic acid.

The above obtained acid is dissolved in 3 ml. of ethyl acetate, filtered and the filtrate treated with an excess of a solution of sodium 2-ethylhexanoate in ethyl acetate. The solid which precipitates is collected by filtration, washed with ethyl acetate and dried under vacuum to afford the disodium salt of 3-(3-methoxyprop-1-(t)-enyl)-7β-(α-carboxy-αphenylacetamido)-ceph-3-em-4-carboxylic acid.

Similarly, by following the same procedure using the products of Example 6 wherein the 7β-substituent is α-(tertbutoxycarbonyl)-α-phenylacetamido, the following free acids and their pharmaceutically acceptable salts, including the disodium salts, are prepared:

3-(3-ethoxyprop-1-(t)-enyl)-7β-(α-carboxy-α-phenylacetamido)-ceph-3-em-4-carboxylic acid, 3-(3-n-propoxyprop-1-(t)-enyl)-7β-(α-carboxy-α-phenylacetamido)-ceph-3-em-4-carboxylic acid, 3-(3-isopropoxyprop-1-(t)-enyl)-7β-(α-carboxy-α-phenylacetamido)-ceph-3-em-4-carboxylic acid, 3-(3-n-butoxyprop-1-(t)-enyl)-7β-(α-carboxy-α-phenylacetamido)-ceph-3-em-4-carboxylic acid, 3-(3-sec-butoxyprop-1-(t)-enyl)-7β-(α-carboxy-α-phenylacetamido)-ceph-3-em-4-carboxylic acid, 3-(3-tert-butoxyprop-1-(t)-enyl)-7β-(α-carboxy-α-phenylacetamido)-ceph-3-em-4-carboxylic acid, 3-[3-(β-bromoethoxy)prop-1-(t)-enyl]-7β-(α-carboxy-α-phenylacetamido)-ceph-3-em-4-carboxylic acid, 3-[3-(β-chloroethoxy)prop-1-(t)-enyl]-7β-(α-carboxy-α-phenylacetamido)-ceph-3-em-4-carboxylic acid, 3-(3-allyloxyprop-1-(t)-enyl)-7β-(α-carboxy-α-phenylacetamido)-ceph-3-em-4-carboxylic acid, 3-(3-propargyloxyprop-1-(t)-enyl)-7β-(α-carboxy-α-phenylacetamido)-ceph-3-em-4-carboxylic acid, 3-(3-cyclopentyloxyprop-1-(t)-enyl)-7β-(α-carboxy-α-phenylacetamido)-ceph-3-em-4-carboxylic acid, and 3-(3-benzyloxyprop-1-(t)-enyl)-7α-(α-carboxy-α-phenylacetamido)-ceph-3-em-4-carboxylic acid.

EXAMPLE 10

This example illustrates step 8 of the process of the invention. In this example, 0.17 g. of benzhydryl 3-(3-methoxyprop-1(t)-enyl)-7β-[α-(tert-butoxycarbonylamino)-α-phenylacetamido]-ceph-3-em-4-carboxylate is stirred for 10 minutes at 0° C in a mixture of 0.5 ml. anisole and 3 ml. of trifluoroacetic acid. The solvents are then removed under reduced pressure to afford the trifluoroacetic acid salt of 3-(3-methoxyprop-1-(t)-enyl)-7β-(α-amino-α-phenylacetamido)ceph-3-em-4-carboxylic acid. The salt is mixed with 0.5 ml. of water and 0.5 ml. of a 25% solution of a water immiscible polymeric amine (sold under the Trademark Amberlite LA-1 (acetate form) by the Rohm & Haas Company of Philiadelphia, Pennsylvania) in methylisobutyl ketone and stirred for 30 minutes at room temperature. The mixture is then filtered and the product washed three times with 5 ml. portions of fresh methylisobutyl ketone and then washed twice with 5 ml. of fresh ethyl acetate and dried under vacuum to afford 3-(3-methoxyprop-1-(t)-enyl)-7β-(α-amino-α-phenylacetamido)-ceph-3-em-4-carboxylic acid.

The above obtained acid is dissolved in water and treated with one equivalent of 0.1 N sodium hydroxide solution. The resulting mixture is then evaporated to dryness and the residue mixed with isopropanol. The solid is collected by filtration, washed several times with isopropanol and then dried under vacuum to afford sodium 3-(3-methoxyprop-1-(t)-enyl)-7β-(α-amino-α-phenylacetamido)-ceph-3-em-4-carboxylate.

Similarly, by following the same procedure using the products of Example 6 wherein the 7β-substituent is α-(tertbutoxycarbonylamino)-α-phenylacetamido α-(tert-butoxycarbonylamino)-α-(4-hydroxyphenyl-)acetamido, the following free acids and their pharmaceutically acceptable salts, including the sodium salts, are prepared:

3-(3-ethoxyprop-1-(t)-enyl)-7β-(α-amino-α-phenylacetamido)-ceph-3-em-4-carboxylic acid, 3-(3-n-propoxyprop-1-(t)-enyl)-7β-(α-amino-α-phenylacetamido)-ceph-3-em-4-carboxylic acid, 3-(3-isopropoxyprop-1-(t)-enyl)-7β-(α-amino-α-phenylacetamido)-ceph-3-em-4-carboxylic acid, 3-(3-n-butoxyprop-1-(t)-enyl)-7β-(α-amino-α-phenylacetamido)-ceph-3-em-4-carboxylic acid, 3-(3-sec-butoxyprop-1-(t)-enyl)-7β-(α-amino-α-phenylacetamido)-ceph-3-em-4-carboxylic acid, 3-(3-tert-butoxyprop-1-(t)-enyl)-7β-(α-amino-α-phenylacetamido)-ceph-3-em-4carboxylic acid, 3-[3-(β-bromoethoxy)prop-1-(t)-enyl]-7β-(α-amino-α-phenylacetamido)-ceph-3-em-4-carboxylic acid, 3-[3-(β-chloroethoxy)prop-1-(t)-enyl]-7β-(α-amino-α-phenylacetamido)-ceph-3-em-4-carboxylic acid, 3-(3-allyloxyprop-1-(t)-enyl)-7β-(α-amino-α-phenylacetamido)-ceph-3em-4-carboxylic acid, 3-(3-propargyloxyprop-1-(t)-enyl)-7β-(α-amino-α-phenylacetamido)-ceph-3-em-4-carboxylic acid, 3-(3-cyclopentyloxyprop-1-(t)-enyl)-7β-(α-amino-α-phenylacetamido)-ceph-3-em-4-carboxylic acid, 3-(3-benzyloxyprop-1-(t)-enyl)-7β-(α-amino-α-phenylacetamido)-ceph-3-em-4-carboxylic acid, 3-(3-methoxyprop-1-(t)-enyl)-7β-[α-amino-α-(4-hydroxyphenyl)acetamido]-ceph-3-em-4-carboxylic acid, 3-(3-ethoxyprop-1-(t)-enyl)-7β-[α-amino-α-(4-hydroxyphenyl)acetamido]-ceph-3-em-4-carboxylic acid, 3-(3-n-propoxyprop-1-(t)-enyl)-7β-[α-amino-α-(4-hydroxyphenyl)acetamido]-ceph-3-em-4-carboxylic acid, 3-(3-isopropoxyprop-1-(t)-enyl)-7β-[α-amino-α-(4-hydroxyphenyl)acetamido]-ceph-3-em-4-carboxylic acid, 3-(3-n-butoxyprop-1-(t)-enyl)-7β-[α-amino-α-(4-hydroxyphenyl)acetamido]-ceph-3-em-4-carboxylic acid, 3-(3-sec-butoxyprop-1-(t)-enyl)-7β-[α-amino-α-(4-hydroxyphenyl)acetamido]-ceph-3-em-4-carboxylic acid, 3-(3-tert-butoxyprop-1-(t)-enyl)-7β-[α-amino-α-(4-hydroxyphenyl)acetamido]-ceph-3-em-4-carboxylic acid, 3-[3-(β-bromoethoxy)prop-1-(t)-enyl]-7β-[α-amino-α-(4-hydroxyphenyl)acetamido]-ceph-3-em-4-carboxylic acid, 3-[3-(β-chloroethoxy)prop-1-(t)-enyl]-7β-[α-amino-α-(4-hydroxyphenyl)acetamido]-ceph-3-em-4-carboxylic acid, 3-(3-allyloxyprop-1-(t)-enyl)-7β-[α-amino-α-(4-hydroxyphenyl)acetamido]-ceph-3-em-4-carboxylic acid, 3-(3-propargyloxyprop-1-(t)-enyl)-7β-[α-amino-α-(4-hydroxyphenyl)acetamido]-ceph-3-em-4-carboxylic acid, 3-(3-cyclopentyloxyprop-1-(t)-enyl)-7β-[α-amino-α-(4-hydroxyphenyl)acetamido]-ceph-3-em-4-carboxylic acid, and 3-(3-benzyloxyprop-1-(t)-enyl)-7β-[α-amino-α-(4-hydroxyphenyl)acetamido]-ceph-3-em-4-carboxylic acid.

EXAMPLE 11

This example illustrates step 8 of the process of the invention. In this example, 0.12 g. of benzhydryl 3-(3-methoxyprop-1-(t)-enyl)-7β-[α-(dichloroacetoxy)-α-phenylacetamido]-ceph-3-em-4-carboxylate is stirred for 2 minutes at 0° C in a mixture of 1 ml. anisole and 6 ml. of trifluoroacetic acid. Thereafter, the solvents are removed under reduced pressure and the resulting residue is dissolved in ethyl acetate and extracted with saturated aqueous sodium bicarbonate. The combined extracts are allowed to stand at room temperature for one hour and then acidified to pH 2 with dilute hydrochloric acid. Thereafter, the solution is extracted with ethyl acetate and the extracts washed, dried, and evaporated to afford 3-(3-methoxyprop-1-(t)-enyl)-7β-(α-hydroxy-α-phenylacetamido)-ceph-3-em-4-carboxylic acid.

The above obtained acid is dissolved in 3 ml. of ethyl acetate, filtered and the filtrate treated with a saturated solution of sodium 2-ethylhexanoate in ethyl acetate until no more precipitate is formed. The solid is collected by filtration, washed with ethyl acetate and dried under vacuum to afford sodium 3-(3-methoxyprop-1-(t)-enyl)-7β-(α-hydroxy-α-phenylacetamido)-ceph-3-em-4-carboxylate.

Similarly, by following the same procedure using the products of Example 6, wherein the 7β-substituent is α-(dichloroacetoxy)-α-phenylacetamido, the following free acids and their pharmaceutically acceptable salts, including the sodium salts, are prepared:

3-(3-ethoxyprop-1-(t)-enyl)-7β-(α-hydroxy-α-phenylacetamido)-ceph-3-em-4-carboxylic acid, 3-(3-n-propoxyprop-1-(t)-enyl)-7β-(α-hydroxy-α-phenylacetamido)-ceph-3-em-4-carboxylic acid, 3-(3-isopropoxyprop-1-(t)-enyl)-7β-(α-hydroxy-α-phenylacetamido)-ceph-3-em-4-carboxylic acid, 3-(3-n-butoxyprop-1-(t)-enyl)-7β-(α-hydroxy-α-phenylacetamido)-ceph-3-em-4-carboxylic acid, 3-(3-sec-butoxyprop-1-(t)-enyl)-7β-(α-hydroxy-α-phenylacetamido)-ceph-3-em-4-carboxylic acid, 3-(3-tert-butoxyprop-1-(t)-enyl)-7β-(α-hydroxy-α-phenylacetamido)-ceph-3-em-4-carboxylic acid, 3-[3-(β-bromoethoxy)prop-1-(t)-enyl]-7β-(α-hydroxy-α-phenylacetamido)-ceph-3-em-4-carboxylic acid, 3-[3-(β-chloroethoxy)prop-1-(t)-enyl]-7β-(α-hydroxy-α-phenylacetamido)-ceph-3-em-4-carboxylic acid, 3-(3-allyloxyprop-1-(t)-enyl)-7β-(α-hydroxy-α-phenylacetamido)-ceph-3-em-4-carboxylic acid, 3-(3-propargyloxyprop-1-(t)-enyl)-7β-(α-hydroxy-α-phenylacetamido)-ceph-3-em-4-carboxylic acid, 3-(3-cyclopentyloxyprop-1-(t)-enyl)-7β-(α-hydroxy-α-phenylacetamido)-ceph-3-em-4-carboxylic acid, and 3-(3-benzyloxyprop-1-(t)-enyl)-7β-(α-hydroxy-α-phenylacetamido)-ceph-3-em-4-carboxylic acid.

EXAMPLE 12

This example illustrates step 9 of the process of the invention. In this example, 5 ml. of trifluoroacetic acid is added to a stirring mixture of 200 mg. of benzhydryl 3-(3-methoxyprop-1-(t)-enyl-7β-aminoceph-3-em-4-carboxylate and 0.5 ml. of anisole at 0° C. After 3 minutes, the mixture is evaporated to dryness affording the crystalline trifluoroacetic acid salt of 3-(3-methoxyprop-1-(t)-enyl)-7β-aminoceph-3-em-4-carboxylic acid. The salt is mixed with 0.5 ml. of water and 0.5 ml. of a 25% solution of a water immiscible polymeric amine (sold under the Trademark Amberlite LA-1 (acetate form) by the Rohm and Haas Company of Philadelphia, Pennsylvania) in methylisobutyl ketone. The mixture is stirred for 1 hour at room temperature and then filtered. The resulting product is washed three times with 5 ml. portions of fresh methylisobutyl ketone; twice with 5 ml. portions of ethyl acetate and then dried under vacuum affording 3-(3-methoxyprop-1-(t)-enyl)-7β-aminoceph-3-em-4-carboxylic acid.

Similarly, by following the same procedure but using other products of Example 5 as starting materials, the following compounds are prepared:

3-(3-ethoxyprop-1-(t)-enyl)-7β-aminoceph-3-em-4-carboxylic acid, 3-(3-n-propoxyprop-1-(t)-enyl)-7β-aminoceph-3-em-4-carboxylic acid, 3-(3-isopropoxyprop-1-(t)-enyl)-7β-aminoceph-3-em-4-carboxylic acid, 3-(3-n-butoxyprop-1-(t)-enyl)-7β-aminoceph-3-em-4-carboxylic acid, 3-(3-sec-butoxyprop-1-(t)-enyl)-7β-aminoceph-3-em-4-carboxylic acid, 3-(3-tert-butoxyprop-1-(t)-enyl)-7β-aminoceph-3-em-4-carboxylic acid, 3-[3-(β-bromoethoxy)prop-1-(t)-enyl]-7β-aminoceph-3-em-4-carboxylic acid, 3-[3-(β-chloroethoxy)prop-1-(t)-enyl]-7β-aminoceph-3-em-4-carboxylic acid, 3-(3-allyloxyprop-1-(t)-enyl)-7β-aminoceph-3-em-4-carboxylic acid, 3-(3-propargyloxyprop-1-(t)-enyl)-7β-aminoceph-3-em-4-carboxylic acid, 3-(3-cyclopentyloxyprop-1-(t)-enyl)-7β-aminoceph-3-em-4-carboxylic acid, and 3-(3-benzyloxyprop-1-(t)-enyl)-7β-aminoceph-3-em-4-carboxylic acid.

EXAMPLE 13

This example illustrates step 10a of the process of the invention. In this example, 0.3 g. of phenylacetyl chloride is added to a stirring mixture of 0.2 g. of 3-(3-methoxyprop-1-(t)-enyl)-7β-aminoceph-3-em-4-carboxylic acid, 10 ml. of acetone and 5 ml. of water containing 0.15 g. of sodium bicarbonate.

The resulting mixture is stirred at −10° C for 30 minutes and then allowed to come to room temperature over a period of 1 hour. The mixture is then diluted with water, washed with ethyl ether, and then brought to pH 2 using dilute aqueous hydrochloric acid. The acidified mixture is extracted twice with ethyl acetate and the combined extracts washed with brine, dried and evaporated to afford 3-(3-methoxyprop-1-(t)-enyl)-7β-(phenylacetamido)-ceph-3-em-4-carboxylic acid.

Similarly, by following the same procedure, but replacing phenylacetyl chloride with 4-pyridylthioacetyl chloride, phenoxyacetyl chloride, trifluoromethylthioacetyl chloride, syn-4-nitrophenylacetyl chloride, 3-chlorophenylacetyl chloride, syn-2-methoxyimino-2-(fur-2-yl)acetyl chloride or 1H-tetrazol-1-yl-acetyl chloride is productive of acid products previously prepared via Example 8.

EXAMPLE 14

This example illustrates steps 10 and 11 of the process of the invention. In this example, 0.56 g. of α-dichloroacetoxyphenylacetyl chloride is added to a stirring mixture of 0.2 g. of 3-(3-methoxyprop-1-(t)-enyl)-7β-aminoceph-3-em-4-carboxylic acid, 10 ml. of acetone and 5 ml. of water containing 0.15 g. of sodium bicarbonate at −20° C. The resulting mixture is stirred at −20° C for 30 minutes and then allowed to come to room temperature over a period of 1 hour. The solution is brought to pH 9 and maintained at that pH for 30 minutes using 5%, wt., aqueous sodium bicarbonate solution as required. The aqueous phase is washed with ethyl ether, then acidified to pH 2 using dilute aqueous hydrochloric acid, and then extracted twice with ethyl acetate. The combined extracts are washed with brine, dried and evaporated to dryness in vacuo. The residue is mixed with a mixture of ethyl ether/hexane 1:1, by vol., and filtered. The collected solid is washed again with ethyl ether/hexane 1:1, by vol., to afford 3-(3-methoxyprop-1-(t)-enyl)-6β-(α-hydroxy-α-phenylacetamido)-ceph-3-em-4-carboxylic acid.

Similarly, by following the same procedure, but using other products of Example 12 as starting materials, is productive of acid products previously prepared via Example 11.

EXAMPLE 15

This example illustrates steps 10 and 11 of the process of the invention. In this example, 0.4 g. of α-(tert-butoxycarbonyl)-α-phenylacetyl chloride is added to a stirring mixture of 0.15 g. of 3-(3-methoxyprop-1-(t)-enyl)-7β-aminoceph-3-em-4-carboxylic acid, 10 ml. of acetone and 5 ml. of water containing 0.15 g. of sodium bicarbonate at 0° C. The resulting mixture is stirred at 0° C. for 30 minutes and then allowed to come to room temperature over a period of 1 hour. The mixture is then diluted with water, washed with ethyl ether, and then adjusted to pH 2 using dilute hydrochloric acid. The mixture is extracted twice with ethyl acetate and the combined extracts washed with water dried and evaporated to afford 3-(3-methoxyprop-1-(t)-enyl)-7β-[α-(tert-butoxycarbonyl)-α-phenylacetamido]-ceph-3-em-4-carboxylic acid.

The above obtained acid is stirred for 30 minutes at 0° C in a mixture of 1 ml. of anisole and 6 ml. of trifluoroacetic acid. Thereafter, the solvents are removed under reduced pressure and the resulting residue washed twice with ether to afford 3-(3-methoxyprop-1-(t)-enyl)-7β-(α-carboxy-α-phenylacetamido)-ceph-3-em-4-carboxylic acid.

Similarly, by following the same procedure but using other products of Example 21 as starting materials, is productive of acid products previously prepared via Example 9.

EXAMPLE 16

This example illustrates steps 10 and 11 of the process of the invention. In this example, 0.45 g. of α-(tert-butoxycarbonylamino)-α-phenylacetyl chloride is added to a stirring mixture of 0.15 g. of 3-(3-methoxyprop-1-(t)-enyl)-7β-aminoceph-3-em-4-carboxylic acid and, 10 ml. of acetone and 5 ml. of water containing 0.15 g. of sodium bicarbonate at 0° C. The resulting mixture is stirred at 0° C. for 30 minutes and the allowed to come to room temperature over a period of 1 hour. The mixture is then diluted with water, washed with ethyl ether and then adjusted to pH 2 using dilute hydrochloric acid. The mixture is extracted twice with ethyl acetate and the combined extracts washed with water, dried and evaporated to afford 3-(3-methoxyprop-1-(t)-enyl)-7β-[α-(tert-butoxycarbonylamino)-α-phenylacetamido]-ceph-3-em-4-carboxylic acid.

The above obtained acid is stirred for 30 minutes at 0° C in a mixture of 1 ml. of anisole and 6 ml. of trifluoroacetic acid. Thereafter, the solvents are removed under reduced pressure and the resulting residue mixed with ethyl ether and the mixture to afford the trifluoroacetic salt of 3-(3-methoxyprop-1-(t)-enyl)-7β-(α-amino-α-phenylacetamido)-ceph-3-em-4-carboxylic acid.

The above obtained salt is stirred for 1 hour with a mixture of 0.5 ml. of water and 0.5 ml. of 25%, wt., suspension of a water immiscible polymeric amine (sold under the Trademark Amberlite LA-1, by Rohm & Haas Company of Philadelphia, Pa.) in methyl isobutyl ketone. The resulting solid is collected by filtration, and then washed with a 1:1, by vol., mixture of water/methyl isobutyl ketone, then with methyl isobutyl ketone, then with ethyl acetate and then dried under vacuum to afford 3-(3-methoxyprop-1-(t)-enyl)-7β-(α-amino-α-phenylacetamido)-ceph-3-em-4-carboxylic acid.

Similarly, by following the same procedure but using other products of Example 12 as starting materials is productive of acid products previously prepared via Example 10.

EXAMPLE 17

This example illustrates reintroduction, if desired, of the C-4 carboxy protecting group in free acids of formulas III" (wherein $R^3$ is hydroxy or carboxy) and IV"'. In this example, a solution of 0.2 g. diphenyldiazomethane in 10 ml. of ethyl acetate is added to a solution of 0.35 g. of 3-(3-methoxyprop-1-(t)-enyl)-7β-(α-hydroxy-α-phenylacetamido)-ceph-3-em-4-carboxylic acid in 100 ml. of ethyl acetate. The solution is stirred at 30° C. for three hours and then evaporated to dryness. The resulting residue is chromatographed on silica gel. Elution with a 90:10:1, by vol., methylene chloride/acetone/acetic acid mixture affords benzhydryl 3-(3-methoxyprop-1-(t)-enyl-7β-(α-hydroxy-α-phenylacetamido)-ceph-3-em-4-carboxylate.

Similarly, by following the same procedure but replacing 3-(3-methoxyprop-1-(t)-enyl)-7β-(α-hydroxy-α-phenylacetamido)-ceph-3-em-4-carboxylic acid with other free acids of formulas III" and IV"', the following C-4 esters are prepared:

benzhydryl 3-(3-ethoxyprop-1-(t)-enyl)-7β-(α-hydroxy-α-phenylacetamido)-ceph-3-em-4-carboxylate, benzhydryl 3-(3-n-propoxyprop-1-(t)-enyl)-7β-(α-hydroxy-α-phenylacetamido)-ceph-3-em-4-carboxylate, benzyhydryl 3-(3-isopropoxyprop-1-(t)-enyl)-7β-(α-hydroxy-α-phenylacetamido)-ceph-3-em-4-carboxylate, benzhydryl 3-(3-n-butoxyprop-1-(t)-enyl)-7β-(α-hydroxy-α-phenylacetamido)-ceph-3-em-4-carboxylate, benzhydryl 3-(3-sec-butoxyprop-1-(t)-enyl)-7β-(α-hydroxy-α-phenylacetamido)-ceph-3-em-4-carboxylate, benzhydryl 3-(3-tert-butoxyprop-1-(t)-enyl)-7β-(α-hydroxy-α-phenylacetamido)-ceph-3-em-4-carboxylate, benzhydryl 3-[3-(β-bromoethoxy)prop-1-(t)-enyl]-7β-(α-hydroxy-α-phenylacetamido)-ceph-3-em-4-carboxylate, benzhydryl 3-[3-(β-chloroethoxy)prop-1-(t)-enyl]-7β-(α-hydroxy-α-phenylacetamido)-ceph-3-em-4-carboxylate, benzhydryl 3-(3-allyloxyprop-1-(t)-enyl)-7β-(α-hydroxy-α-phenylacetamido)-ceph-3-em-4-carboxylate, benzhydryl 3-(3-propargyloxyprop-1-(t)-enyl)-7β-(α-hydroxy-α-phenylacetamido)-ceph-3-em-4-carboxylate, benzhydryl 3-(3-cyclopentyloxyprop-1-(t)-enyl-7β-(α-hydroxy-α-phenylacetamido)-ceph-3-em-4-carboxylate, benzyhydryl 3-(3-benzyloxyprop-1-(t)-enyl)-7β-(α-hydroxy-α-phenylacetamido)-ceph-3-em-4-carboxylate, benzhydryl 3-(3-methoxyprop-1-(t)-enyl)-7β-(α-carboxy-α-phenylacetamido)-ceph-3-em-4-carboxylate, benzhydryl 3-(3-ethoxyprop-1(t)-enyl)-7β-(α-carboxy-α-phenylacetamido)-ceph-3-em-4-carboxylate, benzhydryl 3-(3-n-propoxyprop-1-(t)-enyl)-7β-(α-carboxy-α-phenylacetamido)-ceph-3-em-4-carboxylate, benzhydryl 3-(3-isopropoxyprop-1-(t)-enyl)-7β-(α-carboxy-α-phenylacetamido)-ceph-3-em-4-carboxylate, benzhydryl 3-(3-n-butoxyprop-1-(t)-enyl)-7β-(α-carboxy-α-phenylacetamido)-ceph-3-em-4-carboxylate, benzhydryl 3-(3-sec-butoxyprop-1-(t)-enyl)-7β-(α-carboxy-α-phenylacetamido)-ceph-3-em-4-carboxylate, benzhydryl 3-(3-tert-butoxyprop-1-(t)-enyl)-7β-(α-carboxy-α-phenylacetamido)-ceph-3-em-4-carboxylate, benzhydryl 3-[3-(β-bromoethoxy)-prop-1-(t)-enyl]-7β-(α-carboxy-α-phenylacetamido)ceph-3-em-4-carboxylate, benzhydryl 3-[3-(β-chloroethoxy)prop-1-(t)-enyl]-7β-(α-carboxy-α-phenylacetamido)-ceph-3-em-4-carboxylate, benzhydryl 3-(3-allyloxyprop-1-(t)-enyl)-7β-(α-carboxy-α-phenylacetamido)-ceph-3-em-4-carboxylate, benzhydryl 3-(3-propargyloxyprop-1-(t)-enyl)-7β-(α-carboxy-α-phenylacetamido)-ceph-3-em-4-carboxylate, benzhydryl 3-(3-cyclopentyloxyprop-1-(t)-enyl)-7β-(α-carboxy-α-phenylacetamido)-ceph-3-em-4-carboxylate, benzhydryl 3-(3-benzyloxyprop-1-(t)-enyl)-7β-(α-carboxy-α-phenylacetamido)-ceph-3-em-4-carboxylate, benzhydryl 3-(3-methoxyprop-1-(t)-enyl)-7β-(α-amino-α-phenylacetamido)-ceph-3-em-4-carboxylate, benzhydryl 3-(3-ethoxyprop-1-(t)-enyl)-7β-(α-amino-α-phenylacetamido)-ceph-3-em-4-carboxylate, benzhydryl 3-(3-n-propoxyprop-1-(t)-enyl)-7β-(α-amino-α-phenylacetamido)-ceph-3-em-4-carboxylate, benzhydryl 3-(3-isopropoxyprop-1-(t)-enyl)-7β-(α-amino-α-phenylacetamido)-ceph-3-em-4-carboxylate, benzhydryl 3-(3-n-butoxyprop-1-(t)-enyl)-7β-(α-amino-α-phenylacetamido)-ceph-3-em-4-carboxylate, benzhydryl 3-(3-sec-butoxyprop-1-(t)-enyl)-7β-(α-amino-α-phenylacetamido)-ceph-3-em-4-carboxylate, benzhydryl 3-(3-tert-butoxyprop-1-(t)-enyl)-7β-(α-amino-α-phenylacetamido)-ceph-3-em-4-carboxylate, benzhydryl 3-[3-(β-bromoethoxy)prop-1-(t)-enyl]-7β-(α-amino-α-phenylacetamido)-ceph-3-em-4-carboxylate, benzhydryl 3-[3-(β-chloroethoxy)prop-1-(t)-enyl]-7β-(α-amino-α-phenylacetamido)-ceph-3-em-4-carboxylate, benzhydryl 3-(3-allyloxyprop-1-(t)-enyl)-7β-(α-amino-α-phenylacetamido)-ceph-3-em-4-carboxylate, benzhydryl 3-(3-propargyloxyprop-1-(t)-enyl)-7β-(α-amino-α-phenylacetamido)-ceph-3-em-4-carboxylate, benzhydryl 3-(3-cyclopentyloxyprop-1-(t)-enyl)-7β-(α-amino-α-phenylacetamido)-ceph-3-em-4-carboxylate, benzhydryl 3-(3-benzyloxyprop-1-(t)-enyl)-7β-(α-amino-α-phenylacetamido)-ceph-3-em-4-carboxylate, benzhydryl 3-(3-methoxyprop-1-(t)-enyl)-7β-[α-amino-α-(4-hydroxyphenyl)acetamido]-ceph-3-em-4-carboxylate, benzhydryl 3-(3-ethoxyprop-1-(t)-enyl)-7β-[α-amino-α-(4-hydroxyphenyl)acetamido]-ceph-3-em-4-carboxylate, benzhydryl 3-(3-n-propoxyprop-1-(t)-enyl)-7β-[α-amino-α-(4-hydroxyphenyl)acetamido]-ceph-3-em-4-carboxylate, benzhydryl 3-(3-isopropoxyprop-1-(t)-enyl)-7β-[α-amino-α-(4-hydroxyphenyl)acetamido]-ceph-3-em-4-carboxylate, benzhydryl 3-(3-n-butoxyprop-1-(t)-enyl)-7β-[α-amino-α-(4-hydroxyphenyl)acetamido]-ceph-3-em-4-carboxylate, benzhydryl 3-(3-sec-butoxyprop-1-(t)-enyl)-7β-[α-amino-α-(4-hydroxyphenyl)acetamido]ceph-3-em-4-carboxylate, benzhydryl 3-(3-tert-butoxyprop-1-(t)-enyl)-7β-[α-amino-α-(4-hydroxyphenyl)acetamido]-ceph-3-em-4-carboxylate, benzhydryl 3-[3-(β-bromoethoxy)prop-1-(t)-enyl]-7β-(α-amino-α-(4-hydroxyphenyl)acetamido]-ceph-3-em-4-carboxylate, benzhydryl 3-[3-(β-chloroethoxy)prop-1-(t)-enyl]-7β-[α-amino-α-(4-hydroxyphenyl)acetamido]-ceph-3-em-4-carboxylate, benzhydryl 3-(3-allyloxyprop-1-(t)-enyl)-7β-[α-amino-α-(4-hydroxyphenyl)acetamido]-ceph-3-em-4-carboxylate, benzhydryl 3-(3-propargyloxyprop-1-(t)-enyl)-7β-[α-amino-α-(4-hydroxyphenyl)acetamido]-ceph-3-em-4-carboxylate, benzhydryl 3-(3-cyclopentyloxyprop-1-(t)-enyl)-7β-[α-amino-α-(4-hydroxyphenyl)acetamido]-ceph-3-em-4-carboxylate, and benzhydryl 3-(3-benzyloxyprop-1-(t)-enyl)-7β-[α-amino-α-(4-hydroxyphenyl)acetamido]-ceph-3-em-4-carboxylate.

EXAMPLE 18

For purposes of purifying and isolating the free acids of the invention, a small portion (10 mg.) of the sodium salt product is converted to its corresponding 4-carboxylic acid by dissolving the salt in water, adjusting the pH to 1.5 by addition of dilute hydrochloric acid and extracting twice with ethyl acetate. The combined extracts are washed with brine, dried and evaporated to dryness. The residue is mixed with ethyl ether and the purified 4-carboxylic acid product collected by filtration.

EXAMPLE 19

This example illustrates several methods for preparing the sodium salts of the invention.

A. 3-(3-methoxyprop-1-(t)-enyl-7β-(4-pyridylthioacetamido)-ceph-3-em-4-carboxylic acid is dissolved in ethyl acetate and the sodium salt precipitated by the dropwise addition of a saturated solution of sodium 2-ethylhexanoate in ethyl acetate. The sodium salt is collected by filtration, washed twice with ethyl acetate and dried under vacuum to afford sodium 3-(3-methoxyprop-1-(t)-enyl)-7β-(4-pyridylthioacetamido)-ceph-3-em-4-carboxylate.

Similarly by following the same procedure, the corresponding mono, and where applicable, bis, sodium salts of free acids of formulas III", V" and VI" are prepared.

B. 3-(3-methoxyprop-1-(t)-enyl)-7β-(α-amino-α-phenylacetamido)-ceph-3-em-4-carboxylic acid is dissolved in water and treated with one equivalent of 0.1 N sodium hydroxide solution. The resulting mixture is evaporated to dryness and the residue mixed with isopropanol. The solid is collected by filtration, washed several times with isopropanol and then dried under vacuum to afford sodium 3-(3-methoxyprop-1-(t)-enyl)-7β-(α-amino-α-phenylacetamido)-ceph-3-em-4-carboxylate.

Similarly by following the same procedure, the corresponding sodium salts of other free acids of formula IV" are prepared.

What is claimed is:

1. A compound having the formula:

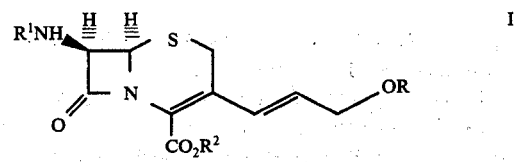

wherein:
R is alkyl having 1 to 4 carbon atoms, β-haloethyl, cyclopentyl or benzyl;
$R^1$ is a group having the formula

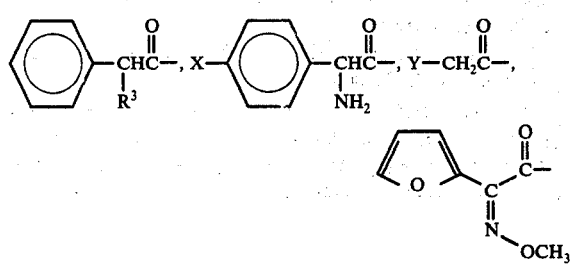

wherein
R³ is hydrogen, hydroxy or carboxy; X is hydrogen or hydroxy; Y is thiophen-2-yl, (1H)-tetrazol-1-yl, 4-pyridylthio, phenoxy, trifluoromethylthio, 4-nitrophenyl or 3-chlorophenyl;

R² is hydrogen or a protecting group selected from the group benzhydryl, benzyl, o-nitrobenzyl, p-nitrobenzyl, 3,5-dinitrobenzyl, p-methoxybenzyl, tert-butyl, pivaloyloxymethyl, phenacyl, and polyhaloalkyl having 2 to 6 carbon atoms; and pharmaceutically acceptable salts thereof.

2. A compound of claim 1 having the formula:

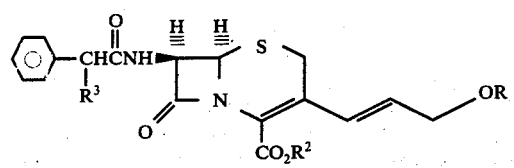

III wherein R, R² and R³ are as defined in claim 1, and pharmaceutically acceptable salts thereof.

3. A compound of claim 2 wherein R² is benzhydryl.
4. A compound of claim 2 wherein R² is hydrogen and pharmaceutically acceptable salts thereof.
5. A compound of claim 4 wherein R is β-bromoethyl.
6. A compound of claim 4 wherein R is methyl.
7. The compound of claim 6 which is 3-(3-methoxyprop-1-(t)-enyl)-7β-(α-carboxy-α-phenylacetamido)-ceph-3-em-4-carboxylic acid and pharmaceutically acceptable salts thereof.
8. The compound of claim 7 wherein said compound is a sodium salt.
9. A compound of claim 1 having the formula:

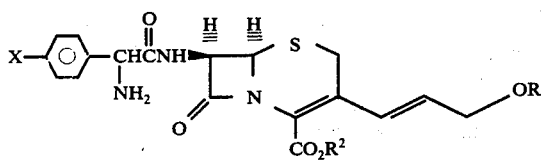

IV wherein R, R² and X are as defined in claim 1, and pharmaceutically acceptable salts thereof.

10. A compound of claim 9 wherein R² is benzhydryl.
11. A compound of claim 9 wherein R² is hydrogen and pharmaceutically acceptable salts thereof.
12. A compound of claim 11 wherein R is β-bromoethyl.
13. A compound of claim 11 wherein R is methyl.
14. The compound of claim 13 which is 3-(3-methoxyprop-1-(t)-enyl)-7β-(α-amino-α-phenylacetamido)-ceph-3-em-4-carboxylic acid and pharmaceutically acceptable salts thereof.
15. The compound of claim 14 wherein said compound is a sodium salt.
16. The compound of claim 13 which is 3-(3-methoxyprop-1-(t)-enyl)-7β-[α-amino-α-(4-hydroxyphenyl)acetamido]-ceph-3-em-4-carboxylic acid and pharmaceutically acceptable salts thereof.

17. The compound of claim 16 wherein said compound is a sodium salt.

18. A compound of claim 1 having the formula:

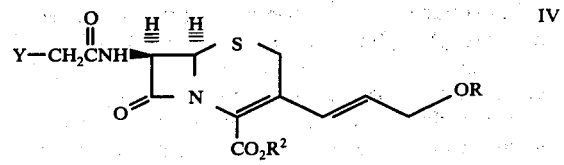

IV wherein R, R² and Y are as defined in claim 1 and pharmaceutically acceptable salts thereof.

19. A compound of claim 18 wherein Y is thiophen-2-yl.
20. A compound of claim 19 wherein R² is benzhydryl.
21. A compound of claim 19 wherein R² is hydrogen and pharmaceutically acceptable salts thereof.
22. A compound of claim 21 wherein R is β-bromoethyl.
23. A compound of claim 21 wherein R is methyl.
24. The compound of claim 23 which is 3-(3-methoxyprop-1-(t)-enyl)-7β-(thiophen-2-ylacetamido)-ceph-3-em-4-carboxylic acid and pharmaceutically acceptable salts thereof.
25. The compound of claim 24 wherein said compound is a sodium salt.
26. A compound of claim 1 having the formula:

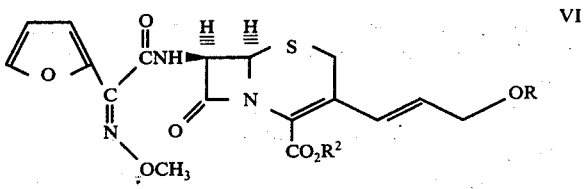

VI wherein R and R² are as defined in claim 1, and pharmaceutically acceptable salts thereof.

27. A compound of claim 26 wherein R² is benzhydryl.
28. A compound of claim 26 wherein R² is hydrogen and pharmaceutically acceptable salts thereof.
29. A compound of claim 28 wherein R is β-bromoethyl.
30. A compound of claim 28 wherein R is methyl.
31. A compound of claim 30 which is 3-(3-methoxyprop-1-(t)-enyl)-7β-[2-methoxyimino-2-(fur-2-yl)acetamido]-ceph-3-em-4-carboxylic acid (syn isomer) and pharmaceutically acceptable salts thereof.
32. The compound of claim 31 wherein said compound is a sodium salt.
33. An antibacterial composition comprising an effective amount of a compound of claim 1 wherein R² is H or a pharmaceutically acceptable salt thereof, and mixtures of such compounds, with a suitable carrier.
34. A method of inhibiting the growth of bacteria which comprises administering to a host object containing or subject to attack by bacteria, an effective amount of a compound of claim 1, wherein R² is hydrogen or a pharmaceutically acceptable salt thereof, or a composition containing same as an active ingredient.

* * * * *